(12) United States Patent
Gottesfeld et al.

(10) Patent No.: US 9,957,225 B2
(45) Date of Patent: May 1, 2018

(54) TREATMENT OF FRIEDREICH'S ATAXIA USING HISTONE DEACETYLASE INHIBITORS

(71) Applicant: The Scripps Research Institute, La Jolla, CA (US)

(72) Inventors: Joel M. Gottesfeld, Del Mar, CA (US); Ann-Kristin Jenssen, Frankfurt am Main (DE); David M. Herman, San Diego, CA (US); Ryan Burnett, San Diego, CA (US); C. James Chou, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days. days.

(21) Appl. No.: 14/480,899

(22) Filed: Sep. 9, 2014

(65) Prior Publication Data
US 2015/0080472 A1    Mar. 19, 2015

Related U.S. Application Data

(63) Continuation of application No. 13/862,727, filed on Apr. 15, 2013, now Pat. No. 8,835,502, which is a continuation of application No. 12/773,032, filed on May 4, 2010, now abandoned, which is a continuation of application No. 11/595,779, filed on Nov. 10, 2006, now abandoned.

(60) Provisional application No. 60/735,483, filed on Nov. 11, 2005, provisional application No. 60/838,906, filed on Aug. 18, 2006, provisional application No. 60/823,051, filed on Aug. 21, 2006.

(51) Int. Cl.
| | |
|---|---|
| *C07C 233/43* | (2006.01) |
| *C07C 233/07* | (2006.01) |
| *C07C 233/25* | (2006.01) |
| *C07D 213/75* | (2006.01) |
| *C07D 215/38* | (2006.01) |
| *C07D 215/40* | (2006.01) |
| *C07C 231/00* | (2006.01) |
| *C07C 233/29* | (2006.01) |
| *C07C 233/44* | (2006.01) |
| *A61K 31/167* | (2006.01) |
| *A61J 1/00* | (2006.01) |
| *C07C 231/02* | (2006.01) |
| *C07C 225/10* | (2006.01) |

(52) U.S. Cl.
CPC .............. *C07C 233/43* (2013.01); *A61J 1/00* (2013.01); *A61K 31/167* (2013.01); *C07C 231/00* (2013.01); *C07C 231/02* (2013.01); *C07C 233/07* (2013.01); *C07C 233/25* (2013.01); *C07C 233/29* (2013.01); *C07C 233/44* (2013.01); *C07D 213/75* (2013.01); *C07D 215/38* (2013.01); *C07D 215/40* (2013.01); *C07C 225/10* (2013.01)

(58) Field of Classification Search
CPC .... A61K 31/167; C07C 225/10; C07C 233/07
See application file for complete search history.

(56) References Cited

U.S. PATENT DOCUMENTS

| | | |
|---|---|---|
| 8,835,502 B2 | 9/2014 | Gottesfeld et al. |
| 2004/0127555 A1* | 7/2004 | Snow .................... C07C 39/15 514/464 |
| 2007/0043076 A1 | 2/2007 | Cai et al. |
| 2007/0219244 A1 | 9/2007 | Jenssen et al. |
| 2011/0021562 A1 | 1/2011 | Jenssen et al. |
| 2013/0210918 A1 | 8/2013 | Gottesfeld et al. |

FOREIGN PATENT DOCUMENTS

| | | |
|---|---|---|
| WO | WO-01/181171 A2 | 3/2001 |
| WO | WO-2001/018171 A2 | 3/2001 |
| WO | WO-03/083067 A2 | 10/2003 |
| WO | WO-2003/083067 A2 | 10/2003 |
| WO | WO-2004/003565 A2 | 1/2004 |
| WO | WO-2007/058927 A1 | 5/2007 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com120031HEALTHIconditions1091241alzheimers.drug.aplindexhtml>.*
"European Application Serial No. 15179699.2, Extended European Search Report dated Feb. 19, 2016", 15 pgs.
Herman, David, et al., "Histone Deacetylase Inhibitors Reverse Gene Silencing in Friedreich's Ataxia", *Nature Chemical Biology*, 2(10), (20/06), 551-558.
Herman, David, et al., "Supplemental synthetic methods and analytical data, Histone deacetylase inhibitors reverse gene silencing in Friedreich's ataxia", *Nature Chemical of Biology*, 2(10), (2006), 11 pgs.
Mai, Antonello, et al., "A New Facile and Expeditious Synthesis of N-Hydroxy-N'-Phenyloctanediamide A Potent Inducer of Terminal Cytodifferentiation", *Organic Preparations and Procedures International*, 33(4), (2001), 391-394.
Shemchuk, L. A., et al., "The Function of Sodium Acetate in Cyclodehydration of Glutaranilic Acids", *Russian Journal of Organic Chemistry*, 34(2), (1998), 231-233.
Sun, Won Suck et al., "Rational Design of an Indolebutanoic Acid Derivative as a Novel Aldose Reductase Inhibitor Based on Docking and 3D QSAR Studies of Phenethylamine Derivatives", *Journal of Medicinal Chemistry*, 46(26), (2003), 5619-5627.
Suzuki, Takayoshi, et al., "Novel Histone Deacetylase Inhibitors: Design, Synthesis, Enzyme Inhibition, and Binding Mode Study of SAHA-Based Non-Hydroxamates", *Bioorganic & Medicinal Chemistry Letters*, 13(24), (2003), 4321-4326.

(Continued)

*Primary Examiner* — Shawquia Jackson
(74) *Attorney, Agent, or Firm* — Schwegman Lundberg & Woessner, P.A.

(57) ABSTRACT

The invention provides methods of treating Friedreich's ataxia and other neurodegenerative or neuromuscular conditions using histone deacetylase inhibitors.

4 Claims, 5 Drawing Sheets

(56) References Cited

OTHER PUBLICATIONS

"U.S. Appl. No. 11/595,779, Final Office Action dated Dec. 4, 2009", 10 pgs.
"U.S. Appl. No. 11/595,779, Non-Final Office Action dated Jul. 29, 2009", 12 pgs.
"U.S. Appl. No. 11/595,779, Preliminary Amendment filed May 23, 2007", 5 pgs.
"U.S. Appl. No. 11/595,779, Response filed Jun. 12, 2009 to Restriction Requirement dated May 12, 2009", 23 pgs.
"U.S. Appl. No. 11/595,779, Response filed Oct. 27, 2009 to Non Final Office Action dated Jul. 29, 2009", 24 pgs.
"U.S. Appl. No. 11/595,779, Restriction Requirement dated May 12, 2009", 11 pgs.
"U.S. Appl. No. 11/595,779, Second Preliminary Amendment filed Mar. 10, 2008", 3 pgs.
"U.S. Appl. No. 12/773,032, Non Final Office Action dated Jan. 15, 2013", 16 pgs.
"U.S. Appl. No. 12/773,032, Preliminary Amendment filed Jul. 22, 2010", 3 pgs.
"U.S. Appl. No. 12/773,032, Response filed Oct. 22, 2012 to Restriction Requirement dated May 22, 2012", 12 pgs.
"U.S. Appl. No. 12/773,032, Restriction Requirement dated May 22, 2012", 11 pgs.
"U.S. Appl. No. 13/862,727, Response filed Mar. 3, 2014 to Non Final Office Action dated Dec. 2, 2013", 15 pgs.
"U.S. Appl. No. 13/862,727, Non Final Office Action dated Dec. 2, 2013", 17 pgs.
"U.S. Appl. No. 13/862,727, Notice of Allowance dated May 12, 2014", 8 pgs.
"European Application Serial No. 06837299.4, Office Action dated Oct. 25, 2010", 3 pgs.
"European Application Serial No. 06837299.4, Office Action dated Dec. 4, 2009", 3 pgs.
"European Application Serial No. 06837299.4, Response filed Feb. 24, 2011 to Office Action dated Oct. 25, 2010", 25 pgs.
"European Application Serial No. 06837299.4, Response filed Mar. 23, 2010 to Office Action dated Dec. 4, 2009", 18 pgs.
"European Application Serial No. 06837299.4, Response filed Aug. 13, 2009 to Office Action dated Apr. 3, 2009", 26 pgs.
"International Application Serial No. PCT/US2006/043745, International Search Report dated Jul. 30, 2007", 8 pgs.
"International Application Serial No. PCT/US2006/043745, Written Opinion dated Jul. 30, 2007", 8 pgs.
"Japanese Application Serial No. 2008-540207, Amended Claims filed Oct. 19, 2009", (w/ English Translation of Amended Claims), 33 pgs.
06837299.4, "European Application Serial No. 06837299.4, Office Action dated Apr. 3, 2009", 4.
Bieliauskas, A. V, et al., "Isoform-selective histone deacetylase inhibitors.", Chem Soc Rev., 37(7), (Jul. 2008), 1402-13.
Bulteau, A. L, et al., "Frataxin acts as an iron chaperone protein to modulate mitochondrial aconitase activity.", Science, 305(5681), (Jul. 9, 2004), 242-5.
Calabrese, V., et al., "Oxidative stress, mitochondrial dysfunction and cellular stress response in Friedreich's ataxia", J Neurol Sci., 233(1-2), (Jun. 15, 2005), 145-62.
Chacon, G. L, et al., "Cytotoxi evaluation of a series of bisalkanoic anilides and bisbenzoyl diamines", Revista De La Sociedad Quimica De Mexico, 47(2), ISSN: 0583-7693, XP008076292, (2003), 186-189.
Chou, C. James, et al., "Pimelic Diphenylamide 106 is a Slow, Tight-binding Inhibitor of Class I Histone Deacetylases", Journal of Biological Chemistry, vol. 283, No. 51, (Dec. 19, 2008), 35402-35409.
De Ruijter, A. J, et al., "Histone deacetylases (HDACs): characterization of the classical HDAC family.", Biochem J., 370(Pt 3), (Mar. 15, 2003), 737-49.
Finnin, M. S, et al., "Structures of a histone deacetylase homologue bound to the TSA and SAHA inhibitors.", Nature, 401(6749), (Sep. 9, 1999), 188-93.

Gao, L., et al., "Cloning and functional characterization of HDAC11, a novel member of the human histone deacetylase family.", J Biol Chem., 277(28), (Jul. 12, 2002), 25748-55.
Herman, D., et al., "Histone deacetylase inhibitors reverse gene silencing in Friedreich's ataxia", Nature Chemical Biology, 2(10), (2006), 551-558.
Herman, David, et al., "Histone deacetylase inhibitors reverse gene silencing in Friedreich's ataxia", Nature Chemical Biology, Advance Online Publication, published by Nature Publishing Group, (Aug. 20, 2006), 1-8.
Kubicova, L., et al., "Synthesis of N,N' -diarylalkanediamides and their antimycobacterial and antialgal activity", Molecules, 5(5), XP002424071, (2000), 714-726.
Lodi, R., et al., "Mitochondrial dysfunction in Friedreich's ataxia: from pathogenesis to treatment perspectives", Tree Radical Research, 36(4), (Apr. 2002), 461-66.
Mai, Antonello, et al., "A New Facile and Expeditioius Synthesis of N-Hydroxy-N'-Phenyloctanediamide, a Potent Inducer of Terminal Cytodifferentiation", OPPI Briefs, vol. 33, No. 4, (2001), 391-3934.
Methot, J. L, et al., "Exploration of the internal cavity of histone deacetylase (HDAC) with selective HDAC1/HDAC2 inhibitors (SHI-1:2).", Bioorg Med Chem Lett., 18(3), (Feb. 1, 2008), 973-8.
Miller, et al., J. Med. Chem., 46, (2003), 5097-5116.
Rai, Myriam, et al., "HDAC Inhibitors Correct Frataxin Deficiency in a Friedrich Ataxia Mouse Model", PLoS ONE, vol. 3, Issue 4, (Apr. 2008), 1-8.
Rai, Myriam, et al., "Two New Pimelic Diphenylamide HDAC Inhibitors Induce Sustained Frataxin Upregulation in Cells from Friedrich's Ataxia Patients and in a Mouse Model", PLoS ONE, vol. 5, Issue 1, (Jan. 2010), 1-8.
Seznec, H., et al., "Friedreich ataxia: the oxidative stress paradox", Hum Mol Genet., 14(4), (Feb. 15, 2005), 463-74.
Suzuki, T., et al., "Novel histone deacetylase inhibitors: design,synthesis,enzyme inhibition, and binding mode study of SAHA-based non-hydroxamates", Bioorganic & Medicinal Chemistry Letters, 13(24), ISSN: 0960-894X, XP002424070, (2003), 4321-4326.
Warner, D., et al., "Synthesis of Pimelic acid and .alpha.-substituted pimelic acid intermediates", Journel of the American Chemical Society,74, ISSN: 0002-7863, XP002424072, (1952), 371-373.
Wong, J. C, et al., "Structural Biasing Elements for In-Cell Histone Deacetylase Paralog Selectivity", J. Am. Chem. Soc., 125, ISSN: 0002-7863, XP002424073, (Apr. 16, 2003), 5586-5587.
Xu, Chunping, et al., "Chemical Probes Identify a Role for Histone Deacetylase 3 in Friedreich's Ataxia Gene Silencing", Chemistry & Biology 16, (Sep. 25, 2009), 980-989.
Jia, Haiqun, et al., "Histone deacetylase (HDAC) inhibitors targeting HDAC3 and HDAC1 ameliorate polyglutamine-elicited phenotypes in model systems of Huntington's disease", Neurobiol Dis. May 2012 ; 46(2): 351-361, (May 2012), 351-361.
Jia, Haiqun, et al., "The Effects of Pharmacological Inhibition of Histone Deacetylase 3 (HDAC3) in Huntington's Disease Mice", PLoS ONE 11(3): e0152498, (Mar. 31, 2016), 1-14.
Soragni, Elisabetta, et al., "Epigenetic Therapy for Friedreich Ataxia", Ann Neurol. Oct. 2014 ; 76(4): 489-508, (Oct. 2014), 489-508.
Thomas, Elizabeth A., et al., "The HDAC inhibitor 4b ameliorates the disease phenotype transcriptional abnormalities in Huntington's disease transgenic mice", PNAS, vol. 105, No. 40, Oct. 7, 2008, 15564-15569, (Oct. 7, 2008), 15564-15569.
"European Application Serial No. 15179699.2, Response filed Oct. 12, 2016 to Extended European Search Report dated Feb. 19, 2016", 4 pgs.
"European Application Serial No. 15179699.2, Response filed Aug. 31, 2017 to European Office Action dated Apr. 21, 2017", 5 pgs.
"European Application Serial No. 15179699.2, European Office Action dated Apr. 21, 2017", 4 pgs.
U.S. Appl. No. 60/735,483, filed Nov. 11, 2005, Histone Deacetylase Inhibitors as Therapeutics for Neurodegenerative Diseases.
U.S. Appl. No. 60/838,908, filed Aug. 18, 2006, Histone Deacetylase Inhibitors as Therapeutics for Neurodegenerative Diseases.

(56) References Cited

OTHER PUBLICATIONS

U.S. Appl. No. 60/823,051, filed Aug. 21, 2006, Histone Deacetylase Inhibitors as Therapeutics for Neurodegenerative Diseases.
U.S. Appl. No. 11/595,779, filed Nov. 10, 2006, Histone Deacetylase Inhibitors as Therapeutics for Neurological Diseases.
U.S. Appl. No. 12/773,032, filed May 4, 2010, Treatment of Friedreich's Ataxia Using Histone Deacetylase Inhibitors.
U.S. Appl. No. 13/862,727, filed Apr. 15, 2013, Treatment of Friedreich's Ataxia Using Histone Deacetylase Inhibitors.

* cited by examiner

TREATMENT OF FRIEDREICH'S ATAXIA USING HISTONE DEACETYLASE INHIBITORS

CROSS REFERENCE TO RELATED APPLICATIONS

This application is a continuation of U.S. patent application Ser. No. 13/862,727, filed Apr. 15, 2013, which is a continuation of U.S. patent application Ser. No. 12/773,032, filed May 4, 2010, which is a continuation of U.S. patent application Ser. No. 11/595,779, filed Nov. 10, 2006, which claims priority from U.S. Provisional Application Ser. No. 60/735,483, filed Nov. 11, 2005; U.S. Provisional Application Ser. No. 60/838,908, filed Aug. 18, 2006; and U.S. Provisional Application Ser. No. 60/823,051, filed Aug. 21, 2006, all of which are specifically incorporated herein by reference in their entireties.

GOVERNMENT FUNDING

This invention was made with Government support under Grant Nos. NS048989, NS055158 and NS055781 awarded by the National Institutes of Health. The United States Government has certain rights in this invention.

TECHNICAL FIELD

The invention relates to histone deacetylase (HDAC) inhibitors and their uses as therapeutics.

BACKGROUND

Friedreich's ataxia (FRDA) is the most prevalent inherited ataxia in Caucasians (see Pandolfo (1999) *Semin. Neurol.* 19:311). Individuals with FRDA have a deficiency of the mRNA encoding frataxin, a highly conserved 210 amino acid nuclear-encoded, mitochondrial protein that is thought to be involved in iron homeostasis, storage and transfer of iron-sulfur clusters to partner proteins such as aconitase (see Bulteau et al. (2004) *Science* 305:242; Seznec et al. (2005) *Hum. Mol. Genet.* 14:463; Calabrese et al. (2005) *J. Neurol. Sci.* 233:145).

Frataxin insufficiency leads to progressive spinocerebellar neurodegeneration resulting in gait and hand in-coordination, slurred speech, muscle weakness and sensory loss with extraneural scoliosis, cardiomyopathy and diabetes. Generally within 15 to 20 years after the first appearance of symptoms, an affected individual is confined to a wheelchair and in later stages, become completely incapacitated. Most affected individuals die in early adulthood of heart disease. Although antioxidant- and iron-chelator-based strategies have been used to treat FRDA, these strategies only treat the symptoms of the disease and not the cause, i.e. frataxin deficiency. Therefore, there is a need to develop molecules that could restore frataxin protein expression for the treatment of a neurological condition such as FRDA.

In addition, the DNA abnormality found in 98% of FRDA patients is the unstable hyper-expansion of a GAA triplet repeat in the first intron of the frataxin gene (see Campuzano et al., *Science* 271:1423 (1996)). Triplet repeat expansion in genomic DNA is associated with many other neurodegenerative and neuromuscular diseases including, without limitation, myotonic dystrophy, spinal muscular atrophy, fragile X syndrome, Huntington's disease, spinocerebellar ataxias, amyotrophic lateral sclerosis, Kennedy's disease, spinal and bulbar muscular atrophy and Alzheimer's disease. Triplet repeat expansion may cause disease by altering gene expression. For example, in Huntington's disease, the spinocerebellar ataxias, fragile X syndrome and myotonic dystrophy, expanded repeats lead to gene silencing. Therefore, there is a need to develop molecules that could restore the normal function of genes in neurological diseases.

SUMMARY OF THE INVENTION

The invention provides small molecules that could be used to treat a neurological disease such as FRDA. The invention provides small molecule inhibitors that are effective in restoring the normal function of a gene, e.g. restoring transcription of frataxin mRNA. The present invention involves the discovery that lymphocytes from FRDA patients that have been incubated with histone deacetylase (HDAC) inhibitors show elevated levels of acetylated histones. In addition, the invention concerns the discovery that the HDAC inhibitor BML-210 and other novel HDAC inhibitors have the effect of increasing frataxin mRNA in lymphocytes from FRDA patients. Accordingly, the invention is directed to pharmaceutical compositions of HDAC inhibitors and their use as therapeutics for chronic and acute neurological diseases such as, for example, Friedreich's ataxia. The invention is also directed to novel HDAC inhibitors, as well as novel methods for their synthesis.

Accordingly, in one embodiment, the invention provides a compound of formula Ia:

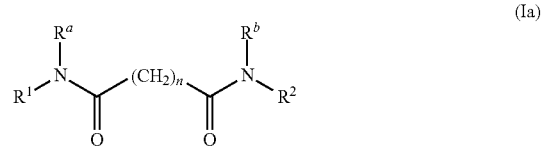

wherein:
n is 2 to about 10;
$R^1$ is aryl or heteroaryl;
$R^2$ is aryl or heteroaryl;
$R^a$ and $R^b$ are each independently H, alkyl, aryl, heteroaryl, or a nitrogen protecting group;
wherein any alkyl, aryl or heteroaryl is optionally substituted with 1 to 3 substituents selected from the group consisting of hydroxy, amino, nitro, cyano, halo, alkyl, trifluoromethyl, alkoxy, aryl, carboxyl, carboxy ester, carboxamide, and $NR^cR^d$;
wherein $R^c$ and $R^d$ are each independently hydrogen, alkyl, or $C(=O)OR^e$ wherein $R^e$ is H or alkyl, and wherein the ester group of the carboxy ester is an alkyl group;
or a salt thereof;
provided that when $R^1$ is phenyl and n is 3-6, $R^2$ is not 2-aminophenyl; and
provided that when $R^1$ is 2-aminophenyl and n is 3-6, $R^2$ is not phenyl.

The compounds of formula Ia are HDAC inhibitors.

In another embodiment, the invention provides methods for preparing compounds of formula I:

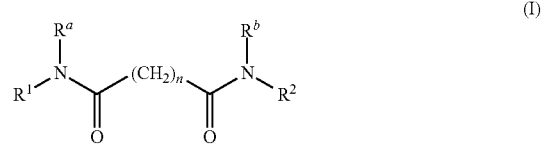

wherein:
n is 2 to about 10;
$R^1$ is aryl or heteroaryl;
$R^2$ is aryl or heteroaryl;
$R^a$ and $R^b$ are each independently H, alkyl, aryl, heteroaryl, or a nitrogen protecting group;
wherein any alkyl, aryl or heteroaryl is optionally substituted with 1 to 3 substituents selected from the group consisting of hydroxy, amino, nitro, cyano, halo, alkyl, trifluoromethyl, alkoxy, aryl, carboxyl, carboxy ester, carboxamide, and $NR^cR^d$;
wherein $R^c$ and $R^d$ are each independently hydrogen, alkyl, or $C(=O)OR^e$ wherein $R^e$ is H or alkyl, and wherein the ester group of the carboxy ester is an alkyl group;
or a salt thereof.

According to the methods of the invention, compounds of formula I may be prepared by contacting a compound of formula V:

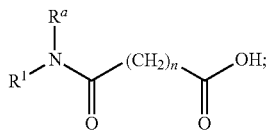

(V)

with one or more coupling agents and a compound of formula VI:

$R^2$—$NH(R^b)$     (VI)

to provide the compound of formula I. The compound of formula V may be prepared by contacting a compound of formula III:

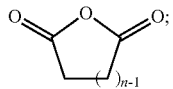

(III)

with a compound of formula IV:

$R^1$—$NH(R^a)$     (IV)

to provide the compound of formula V. The compound of formula III may be prepared by contacting a compound of formula II:

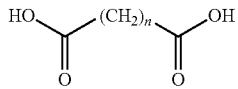

(II)

with a dehydrating agent to provide the compound of formula III.

In another embodiment, the invention provides pharmaceutical compositions that include a compound of formula I in combination with a pharmaceutically acceptable carrier. The pharmaceutical composition may be suitable for oral administration. Pharmaceutical compositions suitable for oral administration can be in the form of a tablet, capsule, or elixir. The pharmaceutical compositions can also be suitable for parenteral administration such as by intravenous, intraperitoneal or subcutaneous administration. The pharmaceutical composition can also be in the form of a sustained-release formulation.

The pharmaceutical compositions can include an amount of the compound of formula I that is effective to increase frataxin mRNA levels in a cell. The cell can be a mammalian cell. The mammalian cell can be a human cell such as a lymphocyte, cardiomyocyte or neuronal cell.

The invention also provides an article of manufacture that includes the compound of formula I contained within packaging materials that have a label indicating that the compound of formula I can be used for treating Friedreich's ataxia.

In another embodiment, the invention provides a method of treating, or preventing or delaying the onset of, a neurodegenerative or neuromuscular condition in a mammal such as a human. The method involves administering to the mammal a compound of formula I in an amount effective to alter the level of histone acetylation in the mammal. The compound of formula I may be administered orally or parenterally. The method may also include identifying the mammal as one suffering from, or at risk for, the neurodegenerative or neuromuscular condition. The neurodegenerative condition may be Huntington's disease, spinocerebellar ataxia, Friedreich's ataxia, Fragile X syndrome, Kennedy's disease, spinal and bulbar muscular atrophy, amyotrophic lateral sclerosis and Alzheimer's disease. The neuromuscular condition may be spinal muscular atrophy or myotonic dystrophy. Thus, in one aspect, the invention provides a method of treating, or preventing or delaying the onset of, Friedreich's ataxia in a mammal. This method involves administering to the mammal a compound of formula I in an amount effective to increase frataxin mRNA in the mammal. The method may include identifying the mammal as one suffering from or at risk for Friedreich's ataxia. A mammal suffering from or at risk for Friedreich's ataxia may be identified by determining the length, extent or number of expansion of a GAA triplet repeat in intron 1 of the frataxin gene. The mammal may also be identified by determining the level of frataxin mRNA or protein.

Definitions

The following definitions are used, unless otherwise described. Specific and preferred values listed below for radicals, substituents, and ranges, are for illustration only; they do not exclude other defined values or other values within defined ranges for the radicals and substituents. Alkyl, alkoxy, alkenyl, and the like denote both straight and branched groups.

As referred to herein, the group "alkyl" refers to a linear or branched hydrocarbon radical that is optionally unsaturated and optionally substituted with functional groups as described herein. The alkyl group can contain from 1 to about 20 carbon atoms. For example and without limiting the scope of the invention, alkyl can be methyl, ethyl, propyl, isopropyl, butyl, iso-butyl, sec-butyl, tert-butyl, pentyl, 3-pentyl, hexyl, heptyl, or octyl. In one embodiment, alkyl is preferably $(C_1-C_8)$alkyl. In another embodiment, alkyl is preferably $(C_1-C_4)$alkyl.

In embodiments where an alkyl group is unsaturated, the alkyl group is an alkenyl group. Alkenyl groups can be, for example, vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 7-octenyl, and branched isomers thereof.

As referred to herein, the group "alkoxy" refers to an optionally substituted alkyl group that is substituted with an oxygen radical. Alkoxy can be, for example, methoxy, ethoxy, propoxy, isopropoxy, butoxy, iso-butoxy, sec-butoxy, pentoxy, 2-pentoxy, 3-pentoxy, or hexyloxy.

As referred to herein, "aryl" refers to a monovalent aromatic hydrocarbon radical of 6-18 carbon atoms derived by the removal of one hydrogen atom from a single carbon atom of a parent aromatic ring system. Aryl groups are typically made up of 6-10 carbon atoms and additionally can possess optional substituents as described herein. Typical aryl groups include, but are not limited to, radicals derived from benzene, naphthalene, anthracene, biphenyl, and the like.

As referred to herein, "heteroaryl" refers to a monocyclic, bicyclic, or tricyclic ring system containing one, two, or three aromatic rings and containing at least one (typically one to about three) nitrogen, oxygen, or sulfur atoms in an aromatic ring. Heteroaryl groups can possess optional substituents as described herein.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl.

In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As referred to herein, "optionally" substituted group refers to the substitution of a group in which one or more hydrogen atoms are each independently replaced with a non-hydrogen substituent. Groups that are optionally substituted are typically substituted with one to five substituents. In other embodiments, optionally substituted groups are substituted with one to three substituents. Typical substituents include, but are not limited to, —X, —R, —O⁻, =O—OR, +S⁻, —SR, —S(=O)R, —S(=O)$_2$R, —S(=O)$_2$O⁻, —S(=O)$_2$OH, —OS(=O)$_2$OR, —S(=O)$_2$NR, —NR$_2$, —N⁺R$_3$, =NR, —N=C=O, —NCS, —NO, —NO$_2$, =N$_2$, —N$_3$, NC(=O)R, —CX$_3$, —C(O)O⁻, —C(=O)R, —C(O)OR, —C(=O)X, —C(=O)NRR, —C(S)R, —C(S)OR, —C(O)SR, —C(S)SR, —C(S)NRR, —C(NR)NRR, —CN, —OCN, —SCN, —OP(=O)(OR)$_2$, —P(=O)(OR)$_2$, —P(=O)(O⁻)$_2$, —P(=O)(OH)$_2$, where each X is independently a halogen (F, Cl, Br, or I); and each R is independently H, alkyl, aryl, a heterocycle, or a protecting group. When the substituent is attached to a group by two bonds (e.g., by a "double bond"), two hydrogen atoms are replaced by the substituent.

As to any of the above groups that contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

As used herein, the term "nitrogen protecting group" refers to any group which, when bound to a nitrogen group, can serve to prevent undesired reactions from occurring at this group and which can be removed by conventional chemical or enzymatic steps to reestablish the free nitrogen (e.g., a —NH— group or a —N= group) at a later stage.

The hydroxyl, carboxyl, amino, and amido groups of the compounds described herein can include optional protecting groups. Suitable protecting groups are known to those skilled in the art. A large number of protecting groups and corresponding chemical cleavage reactions that can be used in conjunction with the compounds of the invention are described in *Protective Groups in Organic Synthesis*, Theodora W. Greene (John Wiley & Sons, Inc., New York, 1991, ISBN 0-471-62301-6), which is incorporated herein by reference in its entirety. Included therein are hydroxyl protecting groups, carboxylic acid protecting groups, and amide-forming groups. In particular, see Chapter 1, Protecting Groups: An Overview, pages 1-20; Chapter 2, Hydroxyl Protecting Groups, pages 21-94; Chapter 4, Carboxyl Protecting Groups, pages 118-154; and Chapter 5, Carbonyl Protecting Groups, pages 155-184. See also Kocienski, Philip J.; *Protecting Groups* (Georg Thieme Verlag Stuttgart, N.Y., 1994), which is incorporated herein by reference in its entirety. Some specific protecting groups that can be employed in preparing the compounds of the invention are discussed below in the section describing the use of protecting groups.

As used herein, a "base" refers to any molecule, ion, or other entity that acts as a proton acceptor. A base can be an organic compound or ion with an unshared electron pair. Typical bases include mono-, di-, and tri-alkyl substituted amines. A base can also be an inorganic compound or ion, such as a metal oxide or metal hydroxide. Bases used in organic synthesis are well known to those of skill in the art. Many bases are disclosed in, for example, the *Aldrich Handbook of Fine Chemicals*, 2003-2004 (Milwaukee, Wis.).

As used herein, "solvent" refers to a substance, usually a liquid, capable of dissolving another substance, e.g., a solid substance, semi-solid substance, or a liquid. Typical solvents include water and organic solvents. It is appreciated by those of skill in the art that the solvent should not chemically react with any of the starting materials or reagents present in the reaction mixture, to any significant degree, under the reaction conditions employed.

As used herein, "solvent system" refers to a medium that includes one or more solvents. A solvent system can be homogeneous (miscible solvents) or heterogeneous (e.g, an organic/aqueous system).

As used herein, "reflux" refers to the process of boiling a liquid solvent system in a vessel, for example, a vessel attached to a condenser, so that the vapors of the solvent system continuously condense for reboiling.

As used herein, "purifying" refers to the process of ridding a substrate (e.g., crystals, an amorphous solid, a liquid, or an oil) of impurities. Suitable methods of purifying include, for example, filtering, washing, recrystallizing and drying, distilling, and chromatography.

As used herein, the terms "isolated" and "purified" refer to substances that are substantially free of other agents, for example, at least about 90%, at least about 95%, at least about 98%, or, at least about 99% pure by weight.

As used herein, "anhydrous" refers to a substance that contains less than about 10 wt. % water, less than about 1 wt. % water, less than about 0.5 wt. % water, less than about 0.1 wt. % water, or less than about 0.01 wt. % water. Anhydrous conditions refer to reaction conditions that have less than about 2 wt. % water, less than about 1 wt. % water, less than about 0.5 wt. % water, less than about 0.1 wt. % water, or less than about 0.01 wt. % water present.

As used herein, "contacting" refers to the act of touching, making contact, or of bringing into immediate proximity. Compounds are typically contacted by forming a solution in a suitable solvent system.

In describing the details of the compounds, compositions, and other limitations, the numerical ranges given herein are those amounts that provide functional results in the composition. Thus, ranges are generally introduced with the term "about" to indicate a certain flexibility in the range. For example, the term "about" can refer to +/− one integer from a given number or the upper or lower limit of range. In other embodiments, the term "about" can refer to +/− two integers from a given number or the upper or lower limit of range. The term "about" can also refer to +/−20% of a given number or numerical range. In other embodiments, the term "about" can refer to +/−10%, or +/−5% of a given number or numerical range. In yet other embodiments, the term "about refers to +/−1%. In still other embodiments, the term "about" refers to exactly the given number or numerical range.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. The present specification provides selected definitions of certain terms, and these definitions are preferred relative to other definitions in the event that there are discrepancies. In addition, the materials, methods, and examples are illustrative only and not intended to be limiting.

Other features and advantages of the invention will be apparent from the following detailed description and from the claims.

BRIEF DESCRIPTION OF DRAWINGS

FIG. 1A shows results from immunoprecipitation (ChIP) experiments performed with the FRDA cell line (GM15850) and the normal cell line (GM15851) using antibodies to the acetylated forms of human histones H3 and H4 (acetylated at the lysine residues indicated). Primer pairs for the frataxin promoter (Pro), and regions immediately upstream (Up) and downstream (Down) of the GAA repeats in the first intron of the frataxin gene were used. Relative recovery, as determined by real-time PCR, is expressed in relation to GAPDH, and the recovery on the Up GAA region for each antibody is set to a value of 100. Error bars are the s.e.m. (standard error of measurement) of 2-3 independent immunoprecipitation, and each immunoprecipitation was quantified in triplicate. FIG. 1B shows ChIP results performed for the region upstream of the GAA repeats using antibodies to histone H3 mono-, di- and tri-methylated at K9 for both the FRDA and normal cell lines. Recovery is expressed as percent of GAPDH.

FIG. 2A shows the effects of histone deacetylase inhibitors on the levels of H3 and H4 acetylation in an FRDA lymphoid cell line (15850B). Cells were either untreated or treated with the indicated compounds for 12 hours prior to isolation of acid soluble nuclear proteins, SDS-PAGE and western blotting with antibodies to total histone H4/H3 or acetylated H4/H3. The fold changes in normalized ratio of AcH4 or AcH3 to total H4 or H3 are shown in the bar graph. FIG. 2B shows relative Frataxin mRNA levels determined by quantitative RT-PCR. All values are normalized to GAPDH mRNA levels, which were unaffected by the HDAC inhibitors. Each of the HDAC inhibitors was tested at the $IC_{50}$ value reported by the commercial supplier, as indicated. Error bars are s.e.m.

FIG. 5A shows that HDAC inhibitor 4b increases histone acetylation at particular H3 and H4 lysines on the frataxin gene. FRDA cells were treated with 4b (5 µM for 96 h) prior to ChIP with the indicated antibodies, and PCR was performed with primers for the region upstream of the GAA repeats. Data are shown for both untreated cell lines and the FRDA cells treated with 4b. Recovery is expressed as percent of GAPDH, and all values are normalized to those for GM15851 cells. FIG. 5B shows that SAHA and TSA do not affect histone acetylation on the frataxin gene. FRDA cells were incubated for 96 hours with 2.5 µM SAHA or 0.1 µM TSA and processed for ChIP as in FIG. 5A. Recovery is expressed relative to untreated GM15850 cells, normalized for GAPDH. Error bars are s.e.m.

DETAILED DESCRIPTION OF THE INVENTION

Figure 1A:
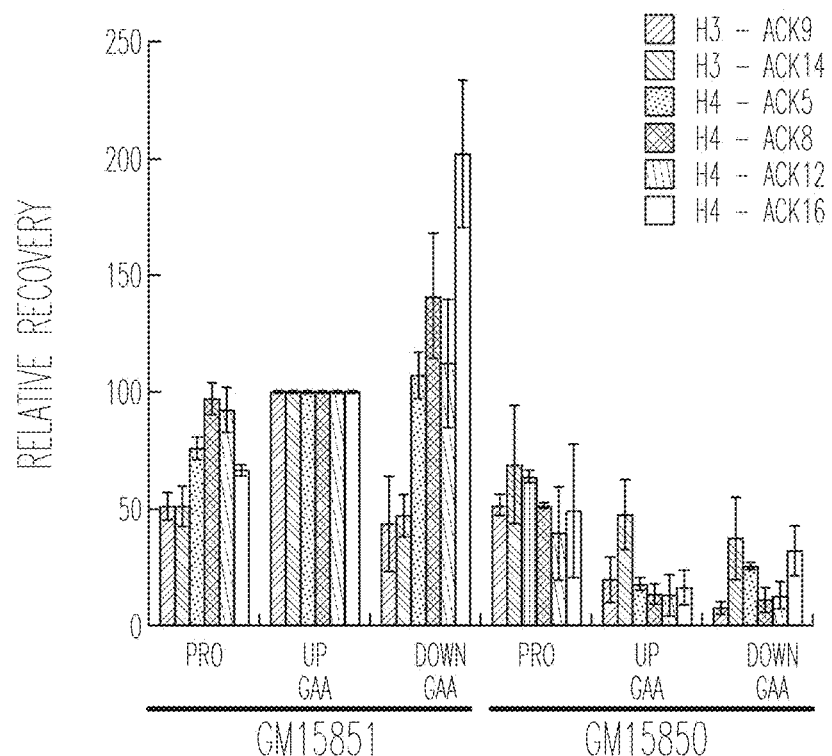
FIG. 1A-1B show bar graphs illustrating the histone modifications on frataxin gene chromatin.

The invention provides small molecules that could be used to treat a neurological condition such as FRDA. The invention concerns the discovery that lymphocytes from FRDA patients that have been incubated with histone deacetylase (HDAC) inhibitors show elevated levels of acetylated histones. In addition, the invention concerns the discovery that the HDAC inhibitors, suberoylanilide orthoaminoanilide (SAOA, BML-210) and pimeloylanilide orthoaminoanilide (PAOA), as well as novel derivatives of SAOA and PAOA, have the effect of increasing frataxin mRNA and protein expression in lymphocytes from FRDA patients. Accordingly, the invention provides pharmaceutical compositions of HDAC inhibitors and their use as therapeutics for chronic and acute neurological diseases such as, for example, Friedreich's ataxia. The invention also provides novel HDAC inhibitors, as well as novel methods for their synthesis.

Histone Deacetylase Inhibitors

The DNA abnormality found in 98% of FRDA patients is the unstable hyper-expansion of a GAA triplet repeat in the first intron of the frataxin gene that results in a defect in transcription of the frataxin gene (see Campuzano et al. (1996) *Science* 271: 1423-7). FRDA patients have a marked deficiency of frataxin mRNA, and longer GAA triplet repeats also cause a more profound frataxin deficiency. FRDA is typical of triplet repeat diseases: normal alleles have 6-34 repeats while FRDA patient alleles have 66-1700 repeats. Longer GAA triplet repeats are associated with earlier onset and increased severity of the disease.

The invention provides for histone deacetylase (HDAC) inhibitors that can restore gene function in a neurological disease that is associated with expansion of a triplet repeat such as FRDA. For example, a HDAC of the invention can increase frataxin mRNA and protein in lymphocytes from FRDA patients. A "histone deacetylase inhibitor" is a small molecule that binds to one or more histone deacetylase (HDAC) to modulate the levels of acetylation of histones, non-histone chromosomal proteins, and other cellular proteins. An HDAC inhibitor of the invention may interact with a HDAC to modulate the level of acetylation of cellular targets.

A histone deacetylase (HDAC) may be any polypeptide having features characteristics of polypeptides that catalyze the removal of the acetyl group (deacetylation) from acetylated target proteins. Features characteristics of HDAC are known in the art, see, for example, Finnin et al. (1999) *Nature* 401: 188. Thus, a HDAC may be a polypeptide that represses gene transcription by deacetylating the ε-amino groups of conserved lysine residues located at the N-termini of histones, e.g. H3, H4, H2A and H2B, that form the nucleosome. HDACs may also deacetylate other proteins such as p53, E2F, α-tubulin and Myo D. See Annemieke et al. (2003) *Biochem. J.* 370: 737. HDAC may also be localized to the nucleus or one that may be found in both the nucleus and cytoplasm.

An HDAC inhibitor of the invention may interact with any HDAC. For example, an HDAC inhibitor of the invention may interact with HDAC from one of the three known classes of HDAC. An HDAC inhibitor of the invention may interact with an HDAC of the class I or class II family of HDAC. Class I HDACs are those that most closely resemble the yeast transcriptional regulator RPD3. Examples of class I HDACs include HDACs 1, 2, 3 and 8, as well as any HDAC that has a deacetylase domain exhibiting from 45% to 93% identity in amino acid sequence to HDACs 1, 2, 3 and 8. Class II HDACs are those that most closely resemble the yeast HDA1 enzyme, and examples of class II HDACs include HDACs 4, 5, 6, 7, 9 and 10. An HDAC inhibitor of the invention may also interact with the NAD$^+$-dependent family of HDACs, which most closely resemble the yeast SIR2 protein. An HDAC inhibitor of the invention may also interact with HDACs that do not fall into one of the above classes, see e.g. Gao et al. (2002) *J. Biol. Chem.* 277: 25748.

Small molecular weight HDAC inhibitors of the invention include SAOA and PAOA, derivatives of SAOA and PAOA described herein and salts thereof. Thus, HDAC inhibitors of the invention include compounds of formula I:

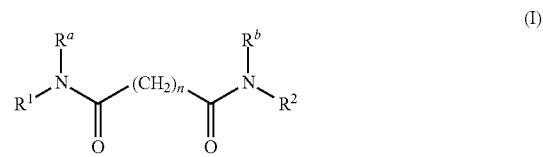

wherein:

n is 2 to about 10;

$R^1$ is aryl or heteroaryl;

$R^2$ is aryl or heteroaryl;

$R^a$ and $R^b$ are each independently H, alkyl, aryl, heteroaryl, or a nitrogen protecting group;

wherein any alkyl, aryl or heteroaryl is optionally substituted with 1 to 3 substituents selected from the group consisting of hydroxy, amino, nitro, cyano, halo, alkyl, trifluoromethyl, alkoxy, aryl, carboxyl, carboxy ester, carboxamide, and $NR^cR^d$;

wherein $R^c$ and $R^d$ are each independently hydrogen, alkyl, or C(=O)$OR^e$ wherein $R^e$ is H or alkyl, and wherein the ester group of the carboxy ester is an alkyl group;

or a salt thereof.

In formula I, the alkyl, aryl or heteroaryl substitutent may be other than carboxyl, carboxy ester, or carboxamide.

In one embodiment, $R^1$ can be aryl. In another embodiment, $R^1$ can be heteroaryl. In other embodiments, $R^1$ can be phenyl, 2-aminophenyl, 3-aminophenyl, 4-aminophenyl, 2-methoxyphenyl, 3-methoxyphenyl, or 4-methoxyphenyl. In other embodiments $R^1$ can be 2-methylphenyl, 3-methylphenyl, or 4-methylphenyl. In other embodiments, $R^1$ can be 2,4-dimethoxyphenyl, 3,5-dimethoxyphenyl, 3,4,5-trimethoxyphenyl, 2,4-diaminophenyl, 3,5-diaminophenyl, or 3,4,5-triaminophenyl. In still other embodiments, $R^1$ can be 2-pyridinyl, 3-quinolinyl, or 8-quinolinyl.

In one embodiment, $R^2$ can be aryl. In another embodiment, $R^2$ can be heteroaryl. In certain embodiments, $R^2$ can be phenyl, 2-aminophenyl, 3-aminophenyl, 4-aminophenyl, 2-methoxyphenyl, 3-methoxyphenyl, or 4-methoxyphenyl. In other embodiments $R^1$ can be 2-methylphenyl, 3-methylphenyl, or 4-methylphenyl. In other embodiments, $R^2$ can be 2,4-dimethoxyphenyl, 3,5-dimethoxyphenyl, 3,4,5-trimethoxyphenyl, 2,4-diaminophenyl, 3,5-diaminophenyl, or 3,4,5-triaminophenyl. In yet another embodiment, $R^2$ can be 2-pyridinyl, 3-quinolinyl, or 8-quinolinyl.

In some embodiments, $R^1$ and $R^2$ can be the same. In other embodiments, $R^1$ and $R^2$ are not the same.

In one embodiment, $R^a$ is H. In another embodiment, $R^b$ is H. In yet another embodiment, $R^a$ is a nitrogen protecting group. In yet another embodiment, $R^b$ can be a nitrogen protecting group.

In one embodiment, n is about 3 to about 6. In another embodiment, n is 5. In yet another embodiment, n is 6.

In one embodiment, $R^1$ can be substituted with one or more substituents. $R^1$ can be substituted with one to about five, or one to about three, substituents. In one embodiment, $R^1$ can be substituted with two amino groups. In another embodiment, $R^1$ can be substituted with two methoxy groups.

In one embodiment, R² can be substituted with one or more substituents. R² can be substituted with one to about five, or one to about three, substituents. In one embodiment, R² can be substituted with two amino groups. In another embodiment, R² can be substituted with two methoxy groups.

Methods of Synthesis of HDAC Inhibitors

The invention also provides novel methods for the synthesis of HDAC inhibitors. For example, compounds of formula I may be prepared by contacting a compound of formula V:

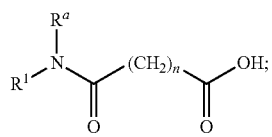
(V)

with one or more coupling agents and a compound of formula VI:

R²—NH(R^b)  (VI)

to provide the compound of formula I. The coupling agents may be 1-(3-dimethylamino-propyl)-3-ethylcarbodiimide hydrochloride (EDC) and 1-hydroxy-7-azabenzotriazole (HOAt). The coupling of compounds of formula V and VI may be carried out in the presence of one or more basic compounds. Suitable basic compounds or "bases" include alkyl amines. The alkyl amine may be tri-alkyl substituted amines, for example, triethylamine or diisopropylethylamine. Hindered amines such as 2,6-lutidine and 2,4,6-collidine may also be used in certain embodiments of the invention.

The coupling of compounds of formula V and VI may be carried out in the presence of a solvent system. Typical solvent systems may be one solvent or more than one solvent. The solvent system may be one or more organic solvents. Two component solvent systems include two solvents that are miscible with one another. The solvent system may dissolve the compounds of formula V and VI to a degree that allows the reaction to proceed to the formation of the compound of formula I. Suitable solvents include dimethylformamide, dimethyl sulfoxide (DMSO), N-methyl pyrrolidone (NMP), tetrahydrofurane (THF), 1,4-dioxane, dichloromethane, and any other suitable non-protic solvent.

The compound of formula I may be isolated and purified. Purification techniques that may be used include precipitation, filtration, recrystallization, and other forms of chromatography including, but not limited to GC, HPLC, reverse phase chromatography, gel plate, thin layer chromatography and the like.

The invention also provides a method of preparing the compound of formula V by contacting a compound of formula III:

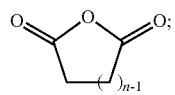
(III)

with a compound of formula IV:

R¹—NH(R^a)  (IV)

to provide the compound of formula V. The compounds of formula III and IV may be contacted in the presence of a solvent system. The solvent system may include one or more organic solvents. Suitable solvents include ether, tetrahydrofuran, and dioxane. In one embodiment, the solvent is tetrahydrofuran.

The invention also provides a method of preparing the compound of formula III by contacting a compound of formula II:

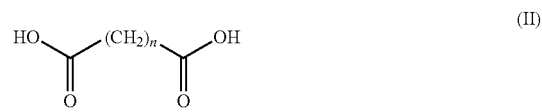
(II)

with a dehydrating agent to provide the compound of formula III. The dehydrating agent may be a carboxylic anhydride. In one embodiment, the carboxylic anhydride is acetic anhydride. Other alkyl or aryl carboxylic anhydrides may also be employed in the reaction. The formation of compounds of formula III are typically carried out under anhydrous conditions. Anhydrous conditions may be achieved by suitable drying of reactants, reagents, and equipment. The compound of formula II and the dehydrating agent may be heated to facilitate the formation of the compound of formula III. The temperature of the reaction may be increased, for example, to about 35° C., to about 40° C., to about 50° C., to about 70° C., or to about 100° C. The temperature of the reaction may also be determined by the temperature at which the solvent system achieves reflux. In such cases, the reaction may be to the reflux temperature of the solvent system employed.

The synthetic protocol for preparing a compound of formula V from a compound of formula II may be illustrated as shown below in Scheme 1:

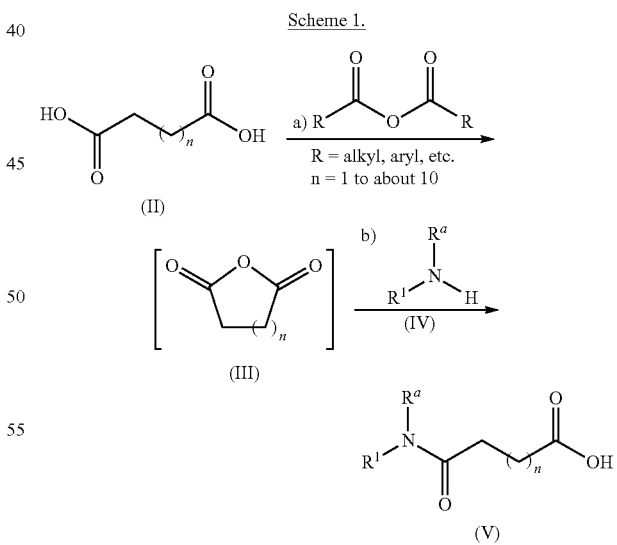

The compound of formula III can be isolated and purified. Alternatively, the compound of formula III can be converted to the compound of formula V directly without purification.

The synthetic protocol for preparing a compound of formula I from a compound of formula V may be illustrated as shown below in Scheme 2:

Scheme 2.

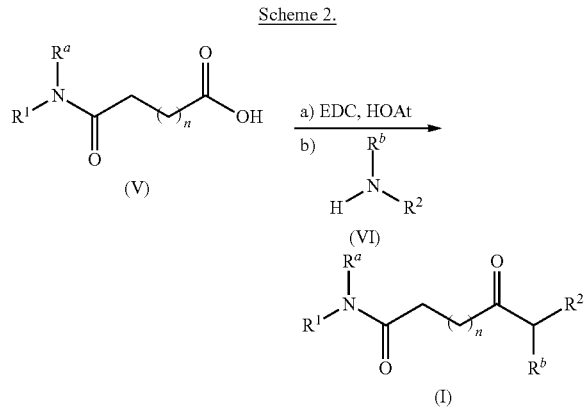

These methods are intended to illustrate the nature of such preparations, not to limit the scope of applicable methods. HDAC inhibitors of the invention may be prepared as described herein or using any other applicable techniques of organic synthesis known in the art. Many applicable techniques not described herein are well known in the art. However, many of the known techniques are elaborated in *Compendium of Organic Synthetic Methods* (John Wiley & Sons, New York), Volumes 1-6; as well as March, J., *Advanced Organic Chemistry*, 3$^{rd}$ Ed. (John Wiley & Sons, New York, 1985), and *Comprehensive Organic Synthesis. Selectivity, Strategy & Efficiency in Modern Organic Chemistry*, in 9 Volumes, Barry M. Trost, Ed.-in-Chief (Pergamon Press, New York, 1993 printing).

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be about −100° C. to about 200° C., solvents will be aprotic or protic depending on the conditions required, and reaction times will be 1 minute to 10 days. Reaction times are adjusted to achieve desired conversions. Work-up of reactions can include removal of solvent to provide crude products, precipitation and filtration, and/or quenching of any unreacted reagents followed by partition between a water/organic layer system (extraction) and separation of the layer containing the product.

Protecting Groups:

The term "protecting group" may refer to any group which, when bound to a hydroxyl, nitrogen, or other heteroatom, prevents undesired reactions from occurring at this group and which can be removed by conventional chemical or enzymatic steps to reestablish the hydroxyl group. The particular removable protecting group employed is not critical and preferred removable hydroxyl and nitrogen protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl or nitrogen functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981, ("Greene") and the references cited therein, and Kocienski, Philip J.; *Protecting Groups* (Georg Thieme Verlag Stuttgart, N.Y., 1994), both of which are incorporated herein by reference in its entirety.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group will be dependent upon the chemistry of the reaction to be protected against (e.g., acidic, basic, oxidative, reductive or other conditions) and the intended direction of the synthesis.

The protecting groups do not need to be, and generally are not, the same if the compound is substituted with multiple protecting groups. In general, protecting groups will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. Some are, for example, included in the discussion of amides, discussed below.

For further detail regarding carboxylic acid protecting groups and other protecting groups for acids, see Greene as set forth below. Such groups include by way of example and not limitation, esters, amides, hydrazides, and the like.

Ether-, Ester-, and Amide-Forming Protecting Groups:

Ester- and Amide-forming groups include: (1) carboxyl ester/amide-forming groups, and (2) sulfur ester-forming groups, such as sulfonate, sulfate, and sulfinate. In its ester-forming role, a protecting group typically is bound to any acidic group such as, by way of example and not limitation, a —CO$_2$H group, thereby resulting in —CO$_2$R$^a$ where R$^a$ is as defined herein. Examples of protecting groups include:

Heterocycle or aryl radicals. These groups optionally can be polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl; and Heterocycle or aryl substituted with halo, R$^a$, alkylene-O—R$^a$, alkoxy, —CN, —NO$_2$, —OH, carboxy, carboxyester, thiol, thioester, haloalkyl (1-6 halogen atoms), alkenyl, or alkynyl. Such groups include 2-, 3- and 4-alkoxyphenyl (C$_1$-C$_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-halophenyl (1 to 5 halogen atoms, $C_1$-$C_{12}$ alkyl including 4-trifluoromethylphenyl), 2-, 3- and 4-cyanophenyl, 2-, 3-, and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl($C_1$-$C_4$ alkyl, including 2-, 3- and 4-ethylsalicylphenyl), 2-,3- and 4-acetylphenyl, 1,8-dihydroxynaphthyl (—$C_{10}H_6$—OH) and aryloxy ethyl[$C_6$-$C_9$ aryl (including phenoxy ethyl)], 2,2'-dihydroxybiphenyl, 2-, 3-, and 4-N,N-dialkylaminophenol, —$C_6H_4CH_2$—$N(CH_3)_2$, trimethoxybenzyl, triethoxybenzyl, 2-alkyl pyridinyl($C_{1-4}$ alkyl); $C_4$-$C_8$ esters of 2-carboxyphenyl; and $C_{1-4}$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, —OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —$CH_2$—$CH_2$—O—$CH_3$ (methoxy ethyl)]; alkyl substituted by any of the groups set forth above for aryl, in particular —OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$); 2-N-morpholino-ethyl; —N-2-propylmorpholino, 2,3-dihydro-6-hydroxyindene, sesamol, catechol monoester, —$CH_2$—$C(O)$—$N(R^1)_2$, —$CH_2$—$S(O)(R^1)$, —$CH_2$—$S(O)_2(R^1)$, —$CH_2$—$CH(OC(O)CH_2R^1)$—$CH_2$ $(OC(O)CH_2R^1)$, cholesteryl, enolpyruvate ($HO_2C$—C(=$CH_2$)—), and glycerol.

Further examples of protecting groups are ester moieties that, for example, can be bonded via an oxygen of the compound of the invention to —C(O)—O—PG' wherein PG' is —$CH_2$—$C(O)$—$N(R^1)_2$, —$CH_2$—$S(O)(R^1)$, —$CH_2$—$S(O)_2(R^1)$, —$CH_2$—O—$C(O)$—$CH_2$—$C_6H_5$, 3-cholesteryl, 3-pyridyl, N-ethylmorpholino, —$CH_2$—O—$C(O)$—$C_6H_5$, —$CH_2$—O—$C(O)$—$CH_2CH_3$, —$CH_2$—O—$C(O)$—$C(CH_3)_3$, —$CH_2$—$CCl_3$, —$C_6H_5$, —NH—$CH_2$—C(O)O—$CH_2CH_3$, —$N(CH_3)$—$CH_2$—$C(O)O$—$CH_2CH_3$, —$NHR^1$, —$CH_2$—O—$C(O)$—$C_{10}H_{15}$, —$CH_2$—O—C(O)—$CH(CH_3)_2$, and —$CH_2$—$CH(OC(O)CH_2R^1)$—$CH_2$—$(OC(O)CH_2R^1)$. Many of these esters can be synthesized by reacting the compound herein having a free hydroxyl (or acid group) with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). Coupling reagents can be used to facilitate linkage of the compound and the protecting group. Other esters can be synthesized by the methods described by Greene, or by other methods well known to those of skill in the art.

Protecting groups also includes "double ester" forming pro-functionalities such as —$CH_2OC(O)OCH_3$, —$CH_2SCOCH_3$, —$CH_2OCON(CH_3)_2$, dihydro-furan-2-one-5-yl, or alkyl- or aryl-acyloxyalkyl groups (linked to oxygen of the acidic group) (see U.S. Pat. No. 4,968,788). Another example is the pivaloyloxymethyl group. Other examples of useful protecting groups are alkylacyloxymethyl esters and their derivatives, including: 2-(adamantine-1-carboxylate)-ethyl, —$CH(CH_2CH_2OCH_3)OC(O)C(CH_3)_3$, —$CH_2OC(O)C_{10}H_{15}$, —$CH_2OC(O)C(CH_3)_3$, —$CH(CH_2OCH_3)OC(O)C(CH_3)_3$, —$CH(CH(CH_3)_2)OC(O)C(CH_3)_3$, —$CH_2OC(O)CH_2CH(CH_3)_2$, —$CH_2OC(O)C_6H_{11}$, —$CH_2OC(O)C_6H_5$, —$CH_2OC(O)C_{10}H_{15}$, —$CH_2OC(O)CH_2CH_3$, —$CH_2OC(O)CH(CH_3)_2$, —$CH_2OC(O)C(CH_3)_3$ and —$CH_2OC(O)CH_2C_6H_5$. Other esters that are suitable for use herein are described in EP 632048.

One or more acidic hydroxyls can be protected. If more than one acidic hydroxyl is protected then the same or a different protecting group can be employed, e.g., the esters may be different or the same, or a mixed amidate and ester may be used.

Typical nitrogen and hydroxy protecting groups described in Greene (pages 14-118) include substituted methyl and alkyl ethers, substituted benzyl ethers, silyl ethers, esters including sulfonic acid esters, carbonates, sulfates, and sulfonates. For example:

ethers (methyl, t-butyl, allyl);

substituted methyl ethers (methoxymethyl, methylthiomethyl, t-butylthiomethyl, (phenyldimethylsilyl) methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl));

substituted ethyl ethers (1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, p-chlorophenyl, p-methoxyphenyl, 2,4-dinitrophenyl, benzyl;

substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-ylmethyl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido);

silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxyphenylsilyl);

esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, p-poly-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate (mesitoate));

carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate);

groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy) butyrate, 2-(methylthiomethoxymethyl)benzoate); miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethylphosphorodiamidate, n-phenylcarbamate, borate, dimethylphosphinothioyl, 2,4-dinitrophenylsulfenate); and sulfonates (sulfate, methanesulfonate (mesylate), benzylsulfonate, tosylate, triflate).

Uses of HDAC Inhibitors of the Invention

HDAC inhibitors of the invention may be used prophylactically or as a treatment for various neurodegenerative or neuromuscular conditions. More specifically, a HDAC inhibitor of the invention may be used to delay or prevent the onset of a neurodegenerative or neuromuscular condition, as well as to treat a mammal suffering from a neurodegenerative or neuromuscular condition. Non-limiting examples of neurodegenerative conditions include, without limitation, fragile X syndrome, Friedreich's ataxia, Huntington's disease, spinocerebellar ataxias, amyotrophic lateral sclerosis, Kennedy's disease, spinal and bulbar muscular atrophy and Alzheimer's disease. Non-limiting examples of neuromuscular conditions include spinal muscular atrophy and myotonic dystrophy.

Mammals, e.g. humans, to which HDAC inhibitors may be administered include those suffering from the conditions discussed above as well as those who are at risk for developing the above conditions. A mammal at risk for developing a neurodegenerative condition may be identified in numerous ways, including, for example, first determining (1) the length, extent or number of repeats of particular nucleic acid sequences in the individual's genome; the degree of acetylation of core histones; or the expression level of a particular mRNA or protein, and then (2) comparing it with that of a normal individual. An individual at risk for developing a neurodegenerative or neuromuscular condition is one who has an aberrant number of repeat of a particular nucleic aid sequence, degree of acetylation of core histones or expression of a particular gene. For example, a mammal at risk for developing Friedreich's ataxia may be identified by determining the length, extent or number of repeats of a GAA triplet in the first intron of the frataxin gene. A mammal would be at risk for Friedreich's ataxia if the above analysis indicates that there are more than 34 repeats of the GAA triplet, for example, if the mammal has more than 66 repeats of the GAA triplet. A mammal at risk for Friedreich's ataxia could also be identified by determining the levels of frataxin mRNA or protein expressed in the mammal. A mammal would be at risk for Friedreich's ataxia if the levels of frataxin mRNA or protein is lower than the level normally observed in a healthy individual such as for example, an unaffected sibling.

The amount of HDAC inhibitor to be administered to the mammal may be any amount appropriate to restore the level of histone acetylation, or the level of mRNA or protein expression, in the afflicted mammal to that typical of a healthy individual such as an unaffected sibling. The amount of the HDAC inhibitor to be administered may be an effective dose or an appropriate fraction thereof. Such amounts will depend on individual patient parameters including age, physical condition, size, weight, the condition being treated, the severity of the condition, and any concurrent treatment. For example, the effective dose range that is necessary to prevent or delay the onset of the neurodegenerative condition may be significantly lower than the effective dose range for inhibiting the progression of the condition being treated. Factors that determine appropriate dosages are well known to those of ordinary skill in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and/or pharmacodynamic models. The precise amount of HDAC inhibitor administered to a patient will be the responsibility of the attendant physician. However, that a patient may insist upon a lower dose or tolerable dose for medical reasons, psychological reasons or for virtually any other reasons.

HDAC inhibitors of the invention may be administered in numerous ways. For example, HDAC inhibitors of the invention may be administered orally, rectally, topically, or by intramuscular, intraperitoneal subcutaneous or intravenous injection. Preferably, the inhibitors are administered orally or by injection. Other routes include intrathecal administration directly into spinal fluid and direct introduction onto, in the vicinity of or within the target cells. The route of administration may depend on the condition being treated and its severity.

HDAC inhibitors of the invention may be administered orally or by injection at a dose of from 0.1 to 30 mg per kg weight of the mammal, preferably 2 to 15 mg/kg weight of the mammal. The dose range for adult humans is generally from 8 to 2,400 mg/day and preferably 35 to 1,050 mg/day. As certain HDAC inhibitors of the invention are long acting, it may be advantageous to administer an initial dose of 70 to 2,400 mg the first day then a lower dose of 20 to 1,200 mg on subsequent days. If the salt of the compound is administered, then the amount of salt administered is calculated in terms of the base.

Pharmaceutical Compositions

HDAC inhibitors may be administered neat or, preferably, as pharmaceutical compositions. Pharmaceutical compositions of the invention include an appropriate amount of the HDAC inhibitor in combination with an appropriate carrier as well as other useful ingredients.

HDAC inhibitors of the invention include the compounds of formula I, and wherein applicable, acceptable salts thereof. Acceptable salts include, but are not limited to, those prepared from the following acids: alkyl, alkenyl, aryl, alkylaryl and alkenylaryl mono-, di- and tricarboxylic acids of 1 to 20 carbon atoms, optionally substituted by 1 to 4 hydroxyls; alkyl, alkenyl, aryl, alkylaryl and alkenylaryl mono-, di- and trisulfonic acids of 1 to 20 carbon atoms, optionally substituted by 1 to 4 hydroxyls; and mineral acids. Examples include hydrochloric; hydrobromic; sulphuric; nitric; phosphoric; maleic; acetic; salicyclic; p-toluenesulfonic; tartaric; citric; methane sulphonic; formic; malonic; succinic; naphthalene-2-sulphonic; and benzenesulphonic acid. Also, pharmaceutically-acceptable salts may be prepared as amine salts, ammonium salts, or alkaline metal or alkaline earth salts, such as sodium, potassium or calcium salts of the carboxylic acid group. These are formed from alkaline metal or alkaline earth metal bases or from amine compounds. In addition, analogs of the foregoing compounds that act as functional equivalents also are intended to be embraced as equivalents and within the scope of the invention.

Pharmaceutical compositions of HDAC inhibitors suitable for oral administration may be in the form of (1) discrete units such as capsules, cachets, tablets or lozenges each containing a predetermined amount of the HDAC inhibitor; (2) a powder or granules; (3) a bolus, electuary or paste; (4) a solution or a suspension in an aqueous liquid or a non-aqueous liquid; or (4) an oil-in-water liquid emulsion or a water-in-oil liquid emulsion. Thus, compositions suitable for topical administration in the mouth, for example buccally or sublingually, include lozenges. Compositions suitable for parenteral administration include aqueous and non-aqueous sterile suspensions or injection solutions. Compositions suitable for rectal administration may be presented as a suppository.

Thus, pharmaceutical compositions of HDAC inhibitors may be formulated using a solid or liquid carrier. The solid or liquid carrier would be compatible with the other ingredients of the formulation and not deleterious to the recipient. If the pharmaceutical composition is in tablet form, then HDAC inhibitor is mixed with a carrier having the necessary compression properties in suitable proportions and compacted in the shape and size desired. If the composition is in powder form, the carrier is a finely divided solid in admixture with the finely divided active ingredient. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. A solid carrier may include one or more substances that may act as flavoring agents, lubricants, solubilizers, suspending agents, fillers, glidants, compression aids, binders or tablet-disintegrating agents. A suitable carrier may also be an encapsulating material.

If the composition is a solution, suspension, emulsion, syrup, elixirs or pressurized compositions, then liquid carriers may be used. In this case, the HDAC inhibitor is dissolved or suspended in a pharmaceutically acceptable liquid carrier. Suitable examples of liquid carriers for oral and parenteral administration include (1) water, (2) alcohols, e.g. monohydric alcohols and polyhydric alcohols such as glycols, and their derivatives, and (3) oils, e.g. fractionated coconut oil and arachis oil. For parenteral administration, the carrier may also be an oily ester such as ethyl oleate and isopropyl myristate. Liquid carriers for pressurized compositions include halogenated hydrocarbon or other pharmaceutically acceptable propellant. The liquid carrier may contain other suitable pharmaceutical additives such as solubilizers; emulsifiers; buffers; preservatives; sweeteners; flavoring agents; suspending agents; thickening agents; colors; viscosity regulators; stabilizers; osmo-regulators; cellulose derivatives such as sodium carboxymethyl cellulose; anti-oxidants; and bacteriostats. Other carriers include those used for formulating lozenges such as sucrose, acacia, tragacanth, gelatin and glycerin as well as those used in formulating suppositories such as cocoa butter or polyethylene glycol.

If the composition is to be administered intravenously or intraperitoneally by infusion or injection, solutions of the HDAC inhibitor may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The composition suitable for injection or infusion may include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium as described above. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the HDAC inhibitor in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the HDAC inhibitor, plus any additional desired ingredient present in the previously sterile-filtered solutions.

Pharmaceutical compositions of the invention may be in unit-dose or multi-dose form or in a form that allows for slow or controlled release of the HDAC inhibitor. Each unit-dose may be in the form of a tablet, capsule or packaged composition such as, for example, a packeted powder, vial, ampoule, prefilled syringe or sachet containing liquids. The unit-dose form also may be the appropriate number of any such compositions in package form. Pharmaceutical compositions in multi-dose form may be in packaged in containers such as sealed ampoules and vials. In this case, the HDAC inhibitor may be stored in a freeze-dried (lyophilized) condition requiring only the addition of a sterile liquid carrier immediately prior to use. In addition, extemporaneous injection solutions and suspensions may be prepared from sterile powders, granules and tablets of the kind previously described.

The invention will be further described in the following examples, which do not limit the scope of the invention described in the claims.

EXAMPLES

Example 1—Materials & Methods

Cell Culture

Epstein Barr virus transformed lymphoblast cell lines GM15850 from a FRDA patient (alleles with 650 and 1030 GAA repeats in the frataxin gene, from the Coriell Cell Repository, Camden, N.J.), and GM15851 from an unaffected sibling (normal range of repeats), were propagated in RPMI 1640 medium with 2 mM L-glutamine and 15% fetal bovine serum at 37° C. in 5% $CO_2$. Cell growth and morphology were monitored by phase contrast microscopy, and viability by trypan blue exclusion. HDAC inhibitors were dissolved in DMSO and added to the culture medium at the concentrations indicated in the table and figure captions, for the indicated times. The final DMSO concentration in the culture medium did not exceed 0.5% (v/v). All control samples were treated with the same concentration of DMSO lacking compounds. The suppliers of the HDAC inhibitors were: valproic acid (VPA), Calbiochem (San Diego, Calif.); trichostatin A (TSA), suberoyl bis-hydroxamic acid (SBHA), suberoylanilide hydroxamic acid (SAHA), and BML-210, Bio-Mol (Plymouth Meeting, Pa.); each tested at the $IC_{50}$ value reported by the supplier, as indicated in the figures.

Real-Time Quantitative RT-PCR

Real-time quantitative RT-PCR analysis was performed essentially as described in Chuma et al., *Hepatology* 37:198-207 (2003) using the following primers for the frataxin gene: 5'-CAGAGGAAACGCTGGACTCT-3'(SEQ ID NO: 1) and 5'-AGCCAGATTTGCTTGTTTGG-3' (SEQ ID NO:2). RNA was standardized by quantification of GAPDH mRNA as described in Pattyn et al., *Nucl. Acids Res.* 31:122-3 (2003), and all values are expressed relative to GAPDH. Quantitative real-time RT-PCR was performed using iScript One-Step RT-PCR kit with SYBR green (BioRad). Statistical analysis was performed on three independent quantitative RT-PCR experiments for each RNA sample, and error bars shown in the figures represent standard errors of the mean.

Western Blot Analysis

Protein levels in HDAC inhibitor-treated and untreated cells were monitored by western blotting with antibodies to histones H3 and H4 (Upstate Biotechnology) or with antibodies to the acetylated versions of these proteins. Histones were purified by acid extraction as described in the protocols provided by Upstate Biotechnology. Antibodies to human frataxin were from Mitoscience (Eugene, Oreg.) and anti-actin antibodies were from Santa Cruz Biotechnology (CA). Total cell extracts were used for frataxin and actin western blots. Signals were detected by chemiluminescence after probing the blot with HRP-conjugated secondary antibody (Supersignal West, Pierce). To quantify the relative levels of proteins, autoradiograms (within the linear response range of X-ray film) were converted into digital images and the signals quantified using Molecular Dynamics ImageQuant software.

Chromatin Immunoprecipitation

Chromatin immunoprecipitation was performed as previously described (see Luo et al. Cell 92:463-73 (1998). For each immunoprecipitation experiment, the amount of lysate corresponding to 25-50 μg of total DNA was incubated with one of the following antibodies (each from Upsate Biotechnology, with the indicated catalogue numbers): anti-acetyl-Histone H3 (06-599), anti-acetyl-Histone H4 (06-598), anti-acetyl-Histone H3-Lys9 (07-352), anti-acetyl-Histone H3-Lys14 (07-353), anti-acetyl-Histone H4-Lys5 (07-327), anti-acetyl-Histone H4-Lys8 (07-328), anti-acetyl-Histone H4-Lys12 (07-595), anti-acetyl-Histone H4-Lys16 (07-329). Samples were quantified in triplicate by real time PCR, using the standard curve method, and error bars shown in the figures represent standard errors of the mean. The primers used in this study were: for the frataxin promoter, 5'-CCCCACATACCCAACTGCTG-3' (SEQ ID NO:3) and 5'-GCCCGCCGCTTCTAAAATTC-3' (SEQ ID NO:4); for the region upstream of the GAA repeats in intron 1 of the frataxin gene, 5'-GAAACCCAAAGAATGGCTGTG-3' (SEQ ID NO:5), and 5'-TTCCCTCCTCGTGAAACACC-3' (SEQ ID NO:6); for the region downstream of the GAA repeats in intron 1 of the frataxin gene, 5'-CTG-GAAAAATAGGCAAGTGTGG-3' (SEQ ID NO:7) and 5'-CAGGGGTGGAAGCCCAATAC-3' (SEQ ID NO:8); and, for GAPDH, 5'-CACCGTCAAGGCTGAGAACG-3' (SEQ ID NO:9) and 5'-ATACCCAAGGGAGCCACACC-3' (SEQ ID NO:10).

Histone Deacetylase Assays

Each of the histone deacetylase inhibitors was assayed with the BioMol AK500 kit to determine $IC_{50}$ values. Samples were processed as described by BioMol and read with a 96-well fluorescence plate reader. A semi-logarithmic plot of the data was analyzed with Kaleidagraph software to obtain the $IC_{50}$ value.

Human Subjects and Primary Lymphocytes

The Friedreich's Ataxia Research Alliance (Arlington, Va.) recruited a series of families with affected individuals and siblings or parents for anonymous blood donation (with a Human Subjects Protocol approved by the Scripps Clinic Human Subjects Committee and by NINDS, with appropriate informed consent). Blood was collected in heparinized Vacutainer tubes (#364680, BD Biosciences) and lymphocytes were isolated by density centrifugation using Ficoll-Paque PLUS (Amersham Biosciences), according to the manufacturer. Lymphocytes were maintained in the same culture medium and conditions as the established cell lines, and HDAC inhibitor treatment was as described above. Cells were treated with HDAC inhibitors after 16 h, and RNA isolated after subsequent 48 h incubation. Under these culture conditions, no increases in cell number were observed.

Example 2—Synthesis of Bis-Amides HDAC Inhibitors by a Novel Two-Step Procedure General Synthetic Procedure Adipic acid 1a (n=3, Scheme 1), pimelic acid 1b (n=4) or suberic acid 1c (n=5) were used as the starting materials for the synthesis of the HDAC inhibitors. The synthetic scheme is as shown below.

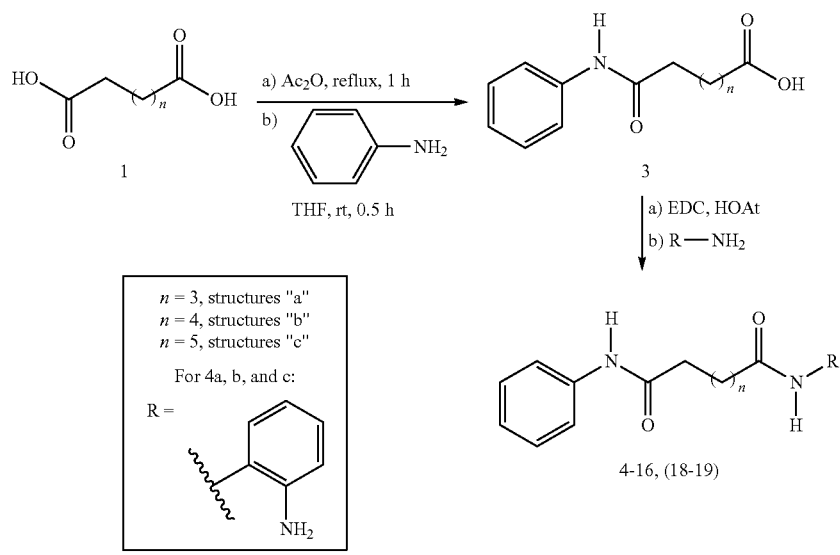

By reaction with acetic anhydride under reflux, the dicarboxylic acids undergo intramolecular ring closure to compounds 2a, 2b and 2c. In contrast to published results (Wong et al., *J. Am. Chem. Soc.* 125:5586-7 (2003)), these anhydrides are further reacted without purification under ring opening conditions with aniline to the precursor compounds 3a, 3b and 3c in about 90% yield. Potent coupling conditions with 1-(3-dimethylamino-propyl)-3-ethylcarbodiimide hydrochloride (EDC) and 1-hydroxy-7-azabenzotriazole (HOAt) produce a high conversion rate, resulting in fast reactions with high yields. By using these conditions the yield of 4b increased to 64% (compared to 33% (Wong et al., *J. Am. Chem. Soc.* 125:5586-7 (2003))). The yield of 4c (equivalent to BML-210) was 50-60% (overall). Comparable yields were obtained for each of the compounds listed in Table 4.

The purity and identity of all compounds were verified by thin layer chromatography, analytical HPLC, MALDI-TOF MS, $^{13}C$- and $^1H$-NMR. NMR spectra were recorded on Varian Mercury 300 or on DRX-500 from Bruker. $^{13}C$ spectra were measured using proton decoupling. All spectra were calibrated to tetramethylsilane. An HPLC system was used for further purification of some compounds (Hitachi L-6200A pump, L4200 UV-VIS detector, D-2500 chromato-integrator, and a Supelcosil PLC-18 (25 cm×21.2 mm, 12 µm) column purchased from Supelco). The RP-HPLC system was set to a flow rate of 5 mL/min in 10% acetonitrile/water/0.1% TFA-100% acetonitrile/0.1% TFA for 0-60 minutes and then 100% acetonitrile/0.1% TFA 10% acetonitrile/water/0.1% TFA for 60-75 minutes. All MALDI-ToF spectra were measured on Voyager System 1089 from Applied Biosystems; α-cyanohydroxy-cinnamic (CHCA) acid was used as matrix. For flash column chromatography, silica gel (mesh 60-200) purchased from J.T. Baker was used. TLC plates were purchased from J.T. Baker (Si250F).

Abbreviations: CHCA (cyano-4-hydroxycinnamic acid), DCM (dichloromethane), diisopropylethylamine (DIPEA), dimethylsulfoxide (DMSO), dimethylformamide (DMF), N-ethyl-N'-(3-dimethylaminopropyl)-carbodiimide hydrochloride (EDC.HCl), 1-hydroxy-1H-benzotriazole hydrate (HOBt), MeOH (methanol), room temperature (r.t), trifluoroacetic acid (TFA), and tetrahydrofurane (THF).

Detailed synthetic methods and analytical data for each compound are as follows. The structures of the precursor compounds, PAOA, SAOA, and various derivatives are provided in the following Tables 1, 2 and 3. Each compound is an embodiment of the invention, by itself or in combination with other components and procedures described herein.

TABLE 1

| | Precursor Compounds | | |
|---|---|---|---|
| Cmpd. No. | Structure | Mol. Wt. | Formula |
| P1 | | 208.26 g/mol | $C_{11}H_{16}N_2O_2$ |
| 3a | | 221.25 g/mol | $C_{12}H_{15}NO_3$ |

TABLE 1-continued

Precursor Compounds

| Cmpd. No. | Structure | Mol. Wt. | Formula |
|---|---|---|---|
| 3b | (phenyl-NH-C(O)-(CH$_2$)$_4$-C(O)OH) | 235.28 g/mol | $C_{13}H_{17}NO_3$ |
| 3b2 | (2-pyridyl-NH-C(O)-(CH$_2$)$_4$-C(O)OH) | 236.27 g/mol | $C_{12}H_{16}N_2O_3$ |
| 3b3 | (2-(Boc-NH)-phenyl-NH-C(O)-(CH$_2$)$_4$-C(O)OH) | 350.41 g/mol | $C_{18}H_{26}N_2O_5$ |
| 3c | (phenyl-NH-C(O)-(CH$_2$)$_5$-C(O)OH) | 249.31 g/mol | $C_{14}H_{19}NO_3$ |

TABLE 2

HDAC Inhibitors

| Cmpd. No. | Structure | Mol. Wt. | Formula |
|---|---|---|---|
| 4a | (phenyl-NH-C(O)-(CH$_2$)$_4$-C(O)-NH-(2-aminophenyl)) | 311.38 g/mol | $C_{18}H_{21}N_3O_2$ |
| 4b (PAOA) | (phenyl-NH-C(O)-(CH$_2$)$_5$-C(O)-NH-(2-aminophenyl)) | 325.43 g/mol | $C_{19}H_{23}N_3O_2$ |

TABLE 2-continued
HDAC Inhibitors
| Cmpd. No. | Structure | Mol. Wt. | Formula |
|---|---|---|---|
| 4c (SAOA) (BML-210) | 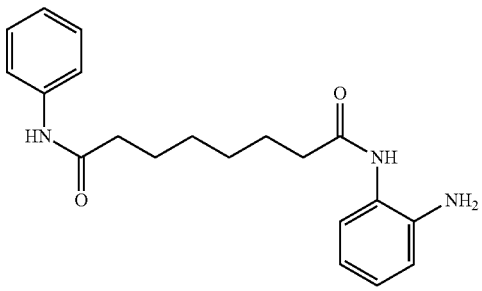 [SMILES: Nc1ccccc1NC(=O)CCCCCCC(=O)Nc1ccccc1] | 339.43 g/mol | $C_{20}H_{25}N_3O_2$ |
| 5b | 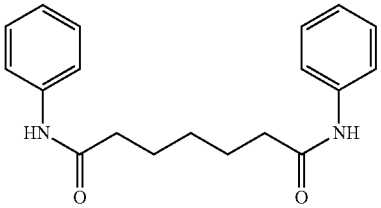 [SMILES: O=C(CCCCCC(=O)Nc1ccccc1)Nc1ccccc1] | 310.39 g/mol | $C_{19}H_{22}N_2O_2$ |
| 6b | 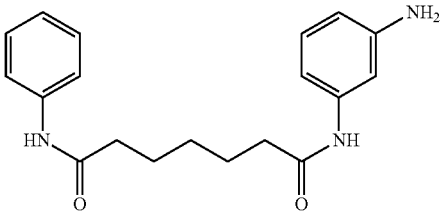 [SMILES: Nc1cccc(NC(=O)CCCCCC(=O)Nc2ccccc2)c1] | 325.43 g/mol | $C_{19}H_{23}N_3O_2$ |
| 6c | 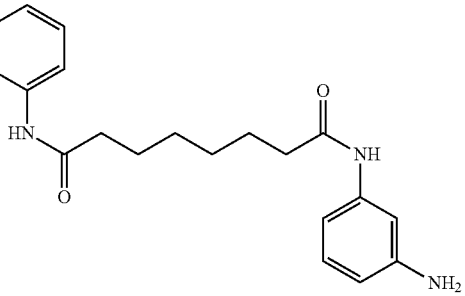 | 339.43 g/mol | $C_{20}H_{25}N_3O_2$ |
| 7b | 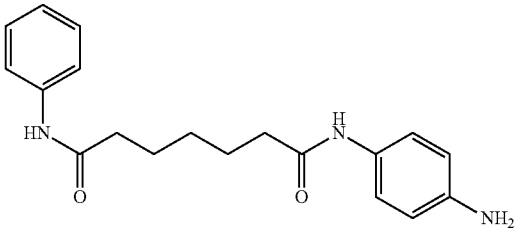 [SMILES: Nc1ccc(NC(=O)CCCCCC(=O)Nc2ccccc2)cc1] | 325.43 g/mol | $C_{19}H_{23}N_3O_2$ |
| 7c | 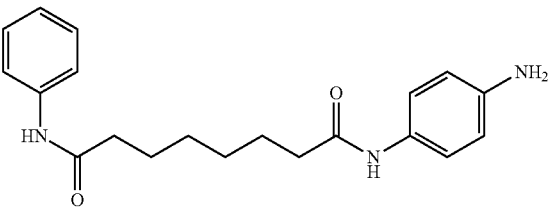 [SMILES: Nc1ccc(NC(=O)CCCCCCC(=O)Nc2ccccc2)cc1] | 339.43 g/mol | $C_{20}H_{25}N_3O_2$ |

TABLE 2-continued
HDAC Inhibitors
| Cmpd. No. | Structure | Mol. Wt. | Formula |
|---|---|---|---|
| 8b | 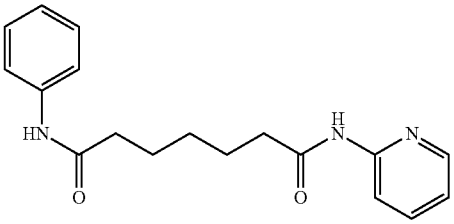 [SMILES: O=C(CCCCCC(=O)Nc1ccccn1)Nc1ccccc1] | 311.38 g/mol | $C_{18}H_{21}N_3O_2$ |
| 8c | 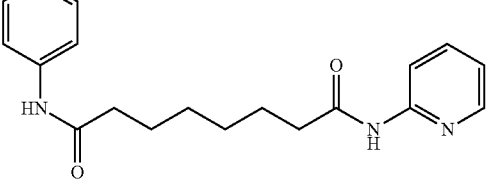 | 325.38 g/mol | $C_{19}H_{23}N_3O_2$ |
| 9b | 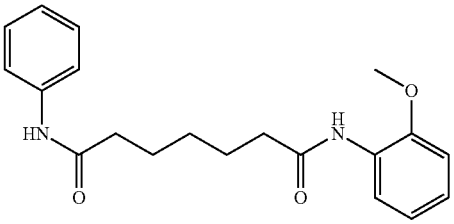 [SMILES: COc1ccccc1NC(=O)CCCCCC(=O)Nc1ccccc1] | 340.42 g/mol | $C_{20}H_{24}N_2O_3$ |
| 9c | 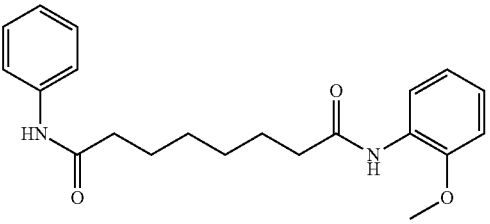 [SMILES: COc1ccccc1NC(=O)CCCCCCC(=O)Nc1ccccc1] | 354.44 g/mol | $C_{21}H_{26}N_2O_3$ |
| 10b | 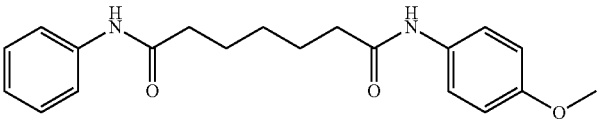 [SMILES: COc1ccc(NC(=O)CCCCCC(=O)Nc2ccccc2)cc1] | 340.42 g/mol | $C_{20}H_{24}N_2O_3$ |
| 11b | 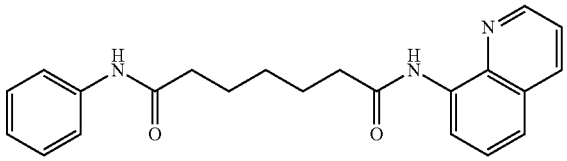 [SMILES: O=C(CCCCCC(=O)Nc1cccc2cccnc12)Nc1ccccc1] | 361.44 g/mol | $C_{22}H_{23}N_3O_2$ |
| 12b | 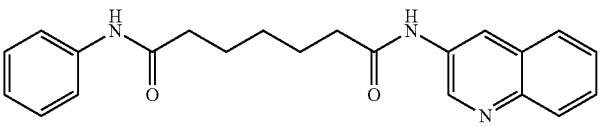 [SMILES: O=C(CCCCCC(=O)Nc1cnc2ccccc2c1)Nc1ccccc1] | 361.44 g/mol | $C_{22}H_{23}N_3O_2$ |
| 13b | 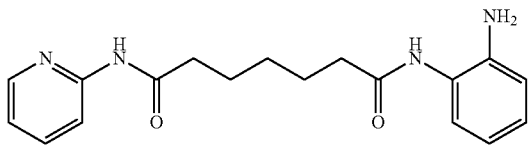 [SMILES: Nc1ccccc1NC(=O)CCCCCC(=O)Nc1ccccn1] | 326.39 g/mol | $C_{18}H_{22}N_4O_2$ |

TABLE 2-continued

HDAC Inhibitors

| Cmpd. No. | Structure | Mol. Wt. | Formula |
|---|---|---|---|
| 14b | 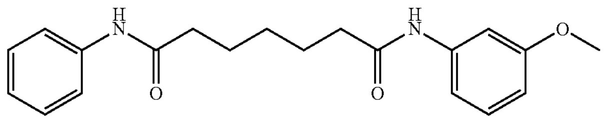 [SMILES: COc1cccc(NC(=O)CCCCCC(=O)Nc2ccccc2)c1] | 340.42 g/mol | $C_{20}H_{24}N_2O_3$ |
| 15b | 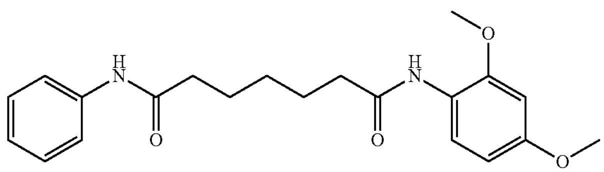 [SMILES: COc1ccc(NC(=O)CCCCCC(=O)Nc2ccccc2)c(OC)c1] | 370.44 g/mol | $C_{21}H_{26}N_2O_4$ |
| 16b | 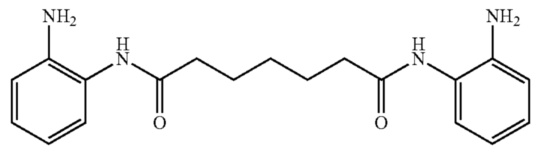 [SMILES: Nc1ccccc1NC(=O)CCCCCC(=O)Nc1ccccc1N] | 340.42 g/mol | $C_{19}H_{24}N_4O_2$ |
| 22a | 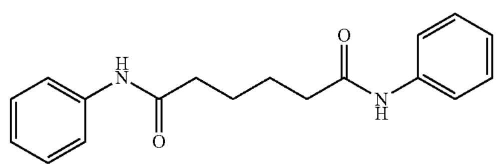 [SMILES: O=C(CCCCC(=O)Nc1ccccc1)Nc1ccccc1] | 296.36 g/mol | $C_{18}H_{20}N_2O_2$ |

Synthesis of the Precursor Compounds

Compound P1: tert-Butyl-2-aminophenylcarbamate

A solution of Di-tert-butyldicarbonate (2.00 g, 10.0 mmol) in DMF (25 mL) was added drop-wise to a stirred solution of 1,2-phenylendiamine (950 mg, 10.0 mmol) in 50 mL DMF at 55° C. After the addition the reaction mixture was stirred for 3 hours. The solvent was removed in vacuo and the residue was taken up in ethylacetate (150 mL). The organic phase was washed three times with sat. NaCl solution (40 mL), dried over $MgSO_4$ and evaporated. The residue was recrystallized from chloroform/n-hexane.

The reaction yielded 1.03 g (4.97 mmol, 49%) of P1 as a pale yellow solid: TLC: $R_f$=0.49 (DCM/MeOH 20:1); $^1$H-NMR (300 MHz, $CDCl_3$): δ =1.51 (s, 9H), 6.35 (m, 1H), 6.72-6.78 (m, 2H), 6.98 (m, 1H), 7.25 (m, 1H).

Compound 3a: 6-Oxo-6-(phenylamino)hexanoic acid

A solution of adipic acid (5.00 g, 34.0 mmol) in acetic anhydride (10 mL) was heated under reflux for 1 hour. After cooling to room temperature, the solvent was removed in vacuo. The crude yellow oil was used without any further purification for the next step. Aniline (3.00 mL, 28.7 mmol) was added to a stirred solution of the produced anhydride in anhydrous THF (10 mL). After stirring at room temperature for 1 hour, the solvent was removed and the residue was recrystallized from water/acetonitrile.

The reaction yielded 2.28 g (10.3 mmol, 36%) of 3a as a colorless solid: TLC: $R_f$=0.48 (DCM/MeOH 20:1); MS (MALDI-ToF, CHCA): m/z (%)=222.2 (100, $[M+H]^+$, calc. 222.2), 244.2 (20, $[M+Na]^+$, calc. 244.2); $^1$H-NMR (300 MHz, DMSO-$D_6$): δ =1.50-1.64 (m, 4H), 2.21-2.34 (m, 4H), 7.00-7.07 (m, 2H), 7.02 (m, $^3J$=7.2 Hz, 1H), 7.28 (m, $^3J$=7.5 Hz, 2H), 7.59-7.62 (m, 2H), 9.90 (s, 1H).

Compound 3b: 7-Oxo-7-(phenylamino)heptanoic acid

A solution of pimelic acid (5.00 g, 31.2 mmol) in acetic anhydride (10 mL) was heated under reflux for 1 hour. After cooling to r.t. the solvent was removed in vacuo. The crude yellow oil was used without any further purification for the next step.

Aniline (3.00 mL, 28.7 mmol) was added to a stirred solution of the produced anhydride in anhydrous THF (10 mL). After stirring at r.t. for 30 minutes, the reaction mixture was diluted with water until a colorless solid precipitated, which was collected by filtration. Recrystallisation from water/acetonitrile gave the pure compound as a colorless solid.

The reaction yielded 3.52 g (15.0 mmol, 48%) of 3a as a colorless solid: TLC: $R_f$=0.68 (DCM/MeOH 9:1); MS (MALDI-ToF, CHCA): m/z (%)=236.3 (100, $[M+H]^+$, calc. 236.1), 258.4 (20, $[M+Na]^+$, calc. 258.1); $^1$H-NMR (500 MHz, DMSO-$D_6$): δ=1.28-1.34 (m, 2H), 1.49-1.62 (m, 4H), 1.55-1.58 (m, 2H), 2.20 (t, $^3J$=9.0 Hz, 2H), 2.30 (t, $^3J$=9.0 Hz, 2H), 7.00 (m, $^3J$=7.5 Hz, 1H), 7.26-7.29 (m, $^3J$=7.5 Hz, 2H), 7.57-7.59 (m, 2H), 9.83 (s, 1H).

Compound 3b2: 7-Oxo-7-(pyridin-2-ylamino)heptanoic acid

A solution of pimelic acid (3.00 g, 18.7 mmol) in acetic anhydride (15 mL) was heated under reflux for 1 hour. After cooling to r.t. the solvent was removed in vacuo. The crude yellow oil was used without any further purification for the next step.

2-Aminopyridine (1.75 g, 18.7 mmol) was added to a stirred solution of the produced anhydride in anhydrous THF (5 mL). After stifling the reaction for 2 hours at r.t., the solvent was removed in vacuo and the residue was triturated with ethylacetate (200 mL). The organic phase was washed with water, saturated NaCl solution and dried over anhydrous $MgSO_4$. After the solvent was removed, the residue was recrystallised from water/trifluoroacetic acid (1:100) to give a colorless solid.

The reaction yielded 1.12 g (4.76 mmol, 25%) of 3b2 as a colorless solid: TLC: $R_f$=0.12 (DCM/MeOH 20:1); MS (MALDI-ToF, CHCA): m/z (%)=237.0 (100, [M+H]$^+$, calc. 237.1); $^1$H-NMR (300 MHz, methanol-$D_4$): δ=1.41-1.50 (m, 2H), 1.60-1.81 (m, 4H), 2.31 (t, $^3$J=7.2 Hz, 2H), 2.56 (t, $^3$J=7.5 Hz, 2H), 7.45 (m, 1H), 7.64 (m, 1H), 8.21-8.28 (m, 1H), 8.32-8.35 (m, 1H).

Compound 3b3: 7-(2-(tert-Butoxycarbonylamino) phenylamino)-7-oxoheptanoic acid

Pimelic acid (160 mg, 1.00 mmol) was refluxed in 5 mL acetic anhydride for 1 hour. The solvent was removed to complete dryness. The residue was diluted in 10 mL dry THF, then P1 (200 mg, 0.96 mmol) in 5 mL dry THF was added drop-wise. The reaction was stirred overnight and then diluted with water. The resulting colorless solid was collected by filtration and recrystallised from ethanol.

The reaction yielded 275 mg (0.78 mmol, 82%) of 3b3 as a colorless solid: TLC: $R_f$=0.23 (DCM/MeOH 20:1); $^1$H-NMR (500 MHz, $CDCl_3$): δ=1.50 (s, 9H), 1.37-1.42 (m, 2H), 1.67-1.72 (m, 4H), 2.31-2.34 (m, 4H), 7.00-7.07 (m, 2H), 7.13 (m, 1H), 7.36 (m, 1H), 8.25 (br. s, 1H).

Compound 3c: 8-Oxo-8-(phenylamino)octanoic acid

A solution of suberic acid (5.00 g, 28.7 mmol) in acetic anhydride (10 mL) was heated under reflux for 1 hour. After cooling to r.t., the solvent was removed in vacuo. The crude yellow oil was used without any further purification for the next step.

Aniline (3.00 mL, 28.7 mmol) was added to a stirred solution of the produced anhydride in anhydrous THF (10 mL). After stirring at r.t. for 30 minutes, the reaction mixture was diluted with water until a colorless solid precipitated, which was collected by filtration. Recrystallisation from water/acetonitrile gave the pure compound as a colorless solid.

The reaction yielded 2.74 g (11.0 mmol, 39%) of 3c as a colorless solid: TLC: $R_f$=0.52 (DCM/MeOH 9:1); MS (MALDI-ToF, CHCA): m/z (%)=250.2 (100, [M+H]$^+$, calc. 250.1), 272.3 (26, [M+Na]$^+$, calc. 272.1); $^1$H-NMR (500 MHz, DMSO-$D_6$): δ=1.27-1.32 (m, 4H), 1.46-1.50 (m, 2H), 1.55-1.58 (m, 2H), 2.18 (t, $^3$J=7.5 Hz, 2H), 2.28 (t, $^3$J=7.5 Hz, 2H), 6.99 (m, $^3$J=7.5 Hz, 1H), 7.25-7.28 (m, $^3$J=7.5 Hz, 2H), 7.56-7.58 (m, $^3$J=7.5 Hz, 2H), 9.82 (m, 1H), 11.9 (s, 1H).

Synthesis of Inhibitors

Compound 4a: $N^1$-(2-Aminophenyl)-$N^7$-phenylhexanediamide

A solution of P1 (86 mg, 0.40 mmol) in DMF (5 ml) was added drop-wise to a stirred solution of 3a (88 mg, 0.40 mmol), EDC.HCl (78 mg, 0.41 mmol), HOBt (64 mg, 0.40 mmol) and DIPEA (68 µl, 0.40 mmol) in DMF (5 mL). After stirring the reaction overnight, water was added until a colorless solid precipitated. The solid was collected by filtration and recrystallized from water/acetonitrile. DCM/TFA (10 ml, 1:1) was added to the dried solid and the solution was stirred for 2 h at r.t. The solvent was removed in vacuo and the residue lyophilized.

The reaction yielded 72 mg (0.17 mmol, 43%) of 4a as a colorless solid: TLC: $R_f$=0.69 (DCM/MeOH 20:1); MS (MALDI-ToF, CHCA): m/z (%)=312.3 (100, [M+H]$^+$, calc. 312.2), 334.4 (2, [M+Na]$^+$, calc. 334.2); $^1$H-NMR (300 MHz, DMSO-$D_6$): δ =1.60-1.67 (m, 4H), 2.32-2.40 (m, 4H), 6.90-7.12 (m, 4H), 7.23-7.30 (m, 3H), 7.58-7.60 (m, 2H), 9.59 (s, 1H), 9.91 (s, 1H).

Compound 4b: $N^1$-(2-Aminophenyl)-$N^7$-phenylheptanediamide

A solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,2-phenylenediamine (432 mg, 4.00 mmol) in DMF (3 mL). After stifling the reaction overnight, water was added until a colorless solid precipitated. The solid was collected by filtration and recrystallised from water/ethanol. The product is further purified by preparative RP-HPLC.

The reaction yielded 60 mg (0.17 mmol, 43%) of 4b as a colorless solid: RP-HPLC: $R_t$=32 minutes; TLC: $R_f$=0.46 (DCM/MeOH 20:1); MS (MALDI-ToF, CHCA): m/z (%)=326.2 (100, [M+H]$^+$, calc. 326.2), 348.2 (40, [M+Na]$^+$, calc. 348.2); $^1$H-NMR (300 MHz, DMSO-$D_6$): δ=1.34-1.38 (m, 2H), 1.58-1.69 (m, 4H), 2.29-2.39 (m, 4H), 6.95-7.15 (m, 4H), 7.23-7.30 (m, 3H), 7.54-7.60 (m, 2H), 9.68 (s, 1H), 9.89 (s, 1H).

Compound 4c: $N^1$-(2-Aminophenyl)-$N^8$-phenyloctanediamide

A solution of compound 3c (100 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,2-phenylenediamine (432 mg, 4.00 mmol) in DMF (3 mL). After stifling the reaction overnight, water was added until a colorless solid precipitated. The solid was collected by filtration and recrystallised from water/ethanol.

The reaction yielded 60 mg (0.17 mmol, 43%) of 4c as a colorless solid: TLC: $R_f$=0.63 (DCM/MeOH 9:1); MS (MALDI-ToF, CHCA): m/z (%)=340.2 (100, [M+H]$^+$, calc. 340.2), 362.2 (15, [M+Na]$^+$, calc. 362.2); $^1$H-NMR (300 MHz, DMSO-$D_6$): δ=1.31-1.32 (m, 4H), 1.56-1.62 (m, 4H), 2.26-2.31 (m, 4H), 6.95-7.15 (m, 4H), 7.22-7.29 (m, 3H), 7.53-7.61 (m, 2H), 9.68 (s, 1H), 9.89 (s, 1H).

Compound 5b: $N^1$-Phenyl-$N^7$-phenylheptanediamide

A solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of aniline (37 mg, 0.40 mmol) in DMF (3 mL). After stirring the reaction overnight, water was added to the reaction mixture until a colorless solid precipitated. The crude product was collected by filtration and recrystallised from water/ethanol.

The reaction yielded 52 mg (0.17 mmol, 42%) of 5b as a colorless solid: TLC: $R_f$=0.46 (DCM/MeOH 20:1); MS (MALDI-ToF, CHCA): m/z (%)=311.1 (100, [M+H]$^+$, calc.

311.2), 333.1 (90, [M+Na]$^+$, calc. 333.3); $^1$H-NMR (500 MHz, DMSO-D$_6$): δ=1.32-1.35 (m, 2H), 1.59-1.64 (m, 4H), 2.31 (t, $^3$J=7.3 Hz, 4H), 7.00 (m, $^3$J=7.3 Hz, 2H), 7.27 (m, $^3$J=7.3 Hz, 4H), 7.57-7.59 (m, 4H), 9.86 (s, 2H).

Compound 6b: N$^1$-(3-Aminophenyl)-N$^7$-phenylheptanediamide

A solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,3-phenylenediamine (432 mg, 4.00 mmol) in DMF (3 mL). After stifling the reaction overnight, the solvent was removed in vacuo. The residue was triturated with ethylacetate/water. The phases were separated and the aqueous phase was extracted two times with ethylacetate (50 mL). The combined organic phases were washed one time with saturated NaCl solution and dried over MgSO$_4$. After evaporation of the solvent, the residue was further purified by flash-chromatography (dichloro-methane/methanol 80:1).

The reaction yielded 24 mg (0.06 mmol, 15%) of 6b as a colorless solid: TLC: R$_f$=0.61 (DCM/MeOH 9:1); MS (MALDI-ToF, CHCA): m/z (%)=326.3 (100, [M+H]$^+$, calc. 326.2), 348.4 (5, [M+Na]$^+$, calc. 348.2); $^1$H-NMR (300 MHz, DMSO-D$_6$): δ=1.24-1.32 (m, 2H), 1.50-1.60 (m, 4H), 2.24 (t, $^3$J=7.5 Hz, 2H), 2.25 (t, $^3$J=7.5 Hz, 2H), 6.68 (m, 1H), 6.94 (m, 1H), 7.11-7.23 (m, 4H), 7.50-7.53 (m, 3H), 9.81 (s, 1H), 9.92 (s, 1H).

Compound 6c: N$^1$-(3-Aminophenyl)-N$^8$-phenyloctanediamide

A solution of compound 3c (100 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,3-phenylenediamine (432 mg, 4.00 mmol) in DMF (3 mL). After stifling the reaction overnight, water was added until a colorless solid precipitated. The solid was collected by filtration and recrystallised from water/ethanol. The product was further purified by RP-HPLC.

The reaction yielded 52 mg (0.15 mmol, 38%) of 6c as a colorless solid: RP-HPLC: R$_t$=36 minutes; TLC: R$_f$=0.66 (DCM/MeOH 9:1); MS (MALDI-ToF, CHCA): m/z (%)=340.3 (100, [M+H]$^+$, calc. 340.2), 362.3 (30, [M+Na]$^+$, calc. 362.2); $^1$H-NMR (300 MHz, DMSO-D$_6$): δ=1.32-1.33 (m, 4H), 1.51-1.65 (m, 4H), 2.26-2.31 (m, 4H), 6.60 (m, 1H), 6.98-7.06 (m, 2H), 7.11-7.17 (m, 1H), 7.23-7.30 (m, 2H), 7.41 (m, 1H), 7.56-7.59 (m, 2H), 9.86 (s, 1H), 9.87 (s, 1H).

Compound 7b: N$^1$-(4-Aminophenyl)-N$^7$-phenylheptanediamide

A solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,4-phenylenediamine (432 mg, 4.00 mmol) in DMF (3 mL). After stifling the reaction overnight, the solvent was removed in vacuo. The residue was triturated with ethylacetate/water. The phases were separated and the aqueous phase was extracted two times with ethylacetate (50 mL). The combined organic phases were washed one time with saturated NaCl solution and dried over MgSO$_4$. After evaporation of the solvent, the residue is recrystallised from water/acetonitrile. The compound was then further purified by RP-HPLC.

The reaction yielded 25 mg (0.06 mmol, 15%) of 7b as a colorless solid: RP-HPLC: R$_t$=30 minutes; TLC: R$_f$=0.38 (DCM/MeOH 9:1); MS (MALDI-ToF, CHCA): m/z (%)=326.4 (100, [M+H]$^+$, calc. 326.2), 348.3 (50, [M+Na]$^+$, calc. 348.2); $^1$H-NMR (300 MHz, DMSO-D$_6$): δ=1.27-1.37 (m, 2H), 1.56-1.66 (m, 4H), 2.24 (m, 4H), 6.98-7.03 (m, 1H), 7.12-7.17 (m, 2H), 7.24-7.29 (m, 2H), 7.56-7.63 (m, 4H), 9.87 (s, 1H), 9.98 (s, 1H).

Compound 7c: N$^1$-(4-Aminophenyl)-N$^8$-phenyloctanediamide

A solution of compound 3c (100 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,4-phenylenediamine (432 mg, 4.00 mmol) in DMF (3 mL). After stirring the reaction overnight, the solvent was removed in vacuo and the slurry was pardoned between water and ethylacetate. The phases were separated and the aqueous phase was extracted two more times with ethylacetate (20 mL). The aqueous phase is then concentrated in vacuo and treated with acetonitrile/water (1:4) until a colorless solid precipitated. The product is isolated by filtration and purified by RP-HPLC.

The reaction yielded 25 mg (0.07 mmol, 16%) of 7c as a colorless solid: RP-HPLC: R$_t$=31 minutes; TLC: R$_f$=0.66 (DCM/MeOH 9:1); MS (MALDI-ToF, CHCA): m/z (%)=340.5 (80, [M+H]$^+$, calc. 340.2), 362.4 (15, [M+Na]$^+$, calc. 362.2); $^1$H-NMR (300 MHz, DMSO-D$_6$): δ=1.25-1.39 (m, 4H), 1.54-1.67 (m, 4H), 2.27 (m, 4H), 7.00-7.09 (m, 1H), 7.14-7.20 (m, 2H), 7.28-7.34 (m, 2H), 7.54-7.65 (m, 4H), 9.78 (s, 1H), 9.95 (s, 1H).

Compound 8b: N$^1$-Phenyl-N$^7$-(pyridin-2-yl)heptanediamide

A solution of 2-aminopyridine (40 mg, 0.40 mmol) in DMF (5 mL) was added dropwise to a cooled solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, water was added to the reaction mixture until a colorless solid precipitated. The product was collected by filtration and recrystallised from water/acetonitrile.

The reaction yielded 80 mg (0.25 mmol, 64%) of 8b as a colorless solid: TLC: R$_f$=0.49 (DCM/MeOH 20:1); MS (MALDI-ToF, CHCA): m/z (%)=312.3 (100, [M+H]$^+$, calc. 312.2), 334.3 (18, [M+Na]$^+$, calc. 334.2); $^1$H-NMR (300 MHz, DMSO-D$_6$): δ=1.29-1.38 (m, 2H), 1.59-1.64 (m, 4H), 2.30 (t, $^3$J=7.5 Hz, 2H), 2.43 (t, $^3$J=7.2 Hz, 2H), 7.00 (m, $^3$J=7.2 Hz, 1H), 7.17 (m, 1H) 7.24-7.29 (m, $^3$J=7.5 Hz, 2H), 7.56-7.59 (m, $^3$J=7.8 Hz, 2H), 7.85-7.98 (m, 2H), 8.30 (m, 1H), 9.86 (s, 1H), 10.8 (s, 1H).

Compound 8c: N$^1$-Phenyl-N$^8$-(pyridin-2-yl)octanediamide

A solution of 2-aminopyridine (40 mg, 0.40 mmol) in DMF (5 mL) was added dropwise to a cooled solution of compound 3c (100 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, water was added to the reaction mixture until a colorless solid precipitated. The product was collected by filtration and recrystallised from water/acetonitrile.

The reaction yielded 23 mg (0.07 mmol, 18%) of 8c as a colorless solid: TLC: $R_f$=0.25 (DCM/MeOH 9:1); MS (MALDI-ToF, CHCA): m/z (%)=326.1 (100, [M+H]$^+$, calc. 326.2), 348.1 (18, [M+Na]$^+$, calc. 348.2); $^1$H-NMR (300 MHz, methanol-D$_4$): δ=1.39-1.46 (m, 4H), 1.59-1.78 (m, 4H), 2.28 (t, $^3$J=7.5 Hz, 2H), 2.54 (t, $^3$J=7.5 Hz, 2H), 7.06 (m, 1H), 7.25-7.30 (m, 2H) 7.42-7.47 (m, 1H), 7.51-7.54 (m, 2H), 7.60 (m, 1H), 8.23 (m, 1H), 8.31 (m, 1H).

Compound 9b: N$^1$-(2-Methoxyphenyl)-N$^7$-phenyl-heptanediamide

A solution of 2-methoxyaniline (50 mg, 0.40 mmol) in DMF (3 mL) was added dropwise to a cooled solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, water was added to the reaction mixture until a colorless solid precipitated. The crude product was collected by filtration and recrystallised from water/acetonitrile.

The reaction yielded 95 mg (0.28 mmol, 70%) of 9b as a colorless solid: TLC: $R_f$=0.27 (DCM/MeOH 20:1); MS (MALDI-ToF, CHCA): m/z (%)=341.4 (100, [M+H]$^+$, calc. 341.2), 363.4 (35, [M+Na]$^+$, calc. 363.2); $^1$H-NMR (300 MHz, DMSO-D$_6$): δ=1.29-1.38 (m, 2H), 1.55-1.67 (m, 4H), 2.30 (t, $^3$J=7.4 Hz, 2H), 2.38 (t, $^3$J=7.4 Hz, 2H), 3.80 (s, 3H), 6.85 (m, 1H), 6.98-7.07 (m, 2H), 7.25-7.30 (m, $^3$J=7.5 Hz, 2H), 7.58-7.60 (m, 2H), 7.93 (m, 1H), 9.03 (s, 1H), 9.86 (s, 1H).

Compound 9c: N$^1$-(2-Methoxyphenyl)-N$^8$-phenyloctanediamide

A solution of 2-methoxyaniline (50 mg, 0.40 mmol) in DMF (3 mL) was added dropwise to a cooled solution of compound 3c (100 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, water was added to the reaction mixture until a colorless solid precipitated. The crude product was collected by filtration and recrystallised from water/acetonitrile.

The reaction yielded 58 mg (0.16 mmol, 41%) of 9c as a colorless solid: TLC: $R_f$=0.61 (DCM/MeOH 9:1); MS (MALDI-ToF, CHCA): m/z (%)=355.4 (100, [M+H]$^+$, calc. 355.2), 377.3 (18, [M+Na]$^+$, calc. 377.2); $^1$H-NMR (300 MHz, DMSO-D$_6$): δ=1.30-1.36 (m, 4H), 1.50-1.68 (m, 4H), 2.30-2.39 (m, 4H), 3.81 (s, 3H), 6.88 (m, 1H), 6.90-7.10 (m, 3H), 7.26-7.30 (m, 2H), 7.58-7.61 (m, 2H), 7.93 (m, 1H), 9.01 (s, 1H), 9.86 (s, 1H).

Compound 10b: N$^1$-(4-Methoxyphenyl)-N$^7$-phenyl-heptanediamide

A solution of 4-methoxyaniline (50 mg, 0.40 mmol) in DMF (5 mL) was added dropwise to a cooled solution of compound 3b (94 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, water was added to the reaction mixture until a colorless solid precipitated. The crude product was collected by filtration and recrystallised from water/acetonitrile.

The reaction yielded 63 mg (0.18 mmol, 46%) of 10b as a colorless solid: TLC: $R_f$=0.38 (DCM/MeOH 20:1); MS (MALDI-ToF, CHCA): m/z (%)=341.4 (100, [M+H]$^+$, calc. 341.2), 363.5 (15, [M+Na]$^+$, calc. 363.2); $^1$H-NMR (300 MHz, DMSO-D$_6$): δ=1.25-1.42 (m, 2H), 1.55-1.73 (m, 4H), 2.27-2.32 (m, 4H), 3.70 (s, 3H), 6.84-6.86 (m, 2H), 7.01 (m, 1H), 7.25-7.30 (m, 2H), 7.48-7.60 (m, 4H), 9.72 (s, 1H), 9.86 (s, 1H).

Compound 11b: N$^1$-Phenyl-N$^7$-(quinolin-8-yl)heptanediamide

A solution of 8-aminoquinoline (58 mg, 0.40 mmol) in 3 mL DMF was added dropwise to a stirred and cooled solution of compound 3b (95 mg, 0.40 mmol), EDC.HCl (78 mg, 0.41 mmol), HOBt (64 mg, 0.40 mmol) and DIPEA (68 µl, 0.40 mmol) in DMF (5 mL). After stirring the reaction overnight, the reaction mixture was diluted with water until a colorless solid precipitated. The solid was collected by filtration, washed with water and recrystallised from water/acetonintrile.

The reaction yielded 34 mg (0.10 mmol, 25%) of 11b as a colorless solid: TLC: $R_f$=0.47 (DCM/MeOH 20:1); MS (MALDI-ToF, CHCA): m/z (%)=362.8 (100, [M+H]$^+$, calc. 362.2), 384.8 (10, [M+Na]$^+$, calc. 384.2); $^1$H-NMR (300 MHz, DMSO-D$_6$): δ=1.36-1.44 (m, 2H), 1.59-1.73 (m, 4H), 2.32 (t, $^3$J=7.4 Hz, 2H), 2.59 (t, $^3$J=7.4 Hz, 2H), 7.00 (m, 1H), 7.23-7.29 (m, 2H), 7.54-7.68 (m, 5H), 8.41 (m, 1H), 8.62 (m, 1H), 8.92 (m, 1H), 9.86 (s, 1H), 10.01 (s, 1H).

Compound 12b: N$^1$-Phenyl-N$^7$-(quinolin-3-yl)heptanediamide

A solution of 3-aminoquinoline (58 mg, 0.40 mmol) in 3 mL DMF was added dropwise to a stirred and cooled solution of compound 3b (95 mg, 0.40 mmol), EDC.HCl (78 mg, 0.41 mmol), HOBt (64 mg, 0.40 mmol) and DIPEA (68 µl, 0.40 mmol) in DMF (5 mL). After stifling the reaction overnight, the reaction mixture was diluted with water until a colorless solid precipitated. The solid was collected by filtration, washed with water and recrystallised from water/acetonitrile.

The reaction yielded 47 mg (0.13 mmol, 32%) of 12b as a colorless solid: TLC: $R_f$=0.47 (DCM/MeOH 20:1); MS (MALDI-ToF, CHCA): m/z (%)=362.7 (100, [M+H]$^+$, calc. 362.2), 384.6 (20, [M+Na]$^+$, calc. 384.2); $^1$H-NMR (300 MHz, DMSO-D$_6$): δ=1.35-1.45 (m, 2H), 1.61-1.75 (m, 4H), 2.34 (t, $^3$J=7.2 Hz, 2H), 2.45 (t, $^3$J=7.5 Hz, 2H), 7.02 (m, 1H), 7.25-7.30 (m, 2H), 7.58-7.61 (m, 2H), 7.67 (m, 1H), 7.76 (m, 1H), 8.02-8.05 (m, 2H), 8.88 (m, 1H), 9.10 (m, 1H), 9.89 (s, 1H), 10.60 (s, 1H).

Compound 13b: N$^1$-(2-Aminophenyl)-N$^7$-(pyridin-2-yl)heptanediamide

A solution of compound 3b2 (95 mg, 0.40 mmol), EDC.HCl (78 mg, 0.41 mmol), HOBt (64 mg, 0.40 mmol) and DIPEA (68 µl, 0.40 mmol) in DMF (5 mL) was added dropwise to a stirred and cooled solution of 1,2-phenylenediamine (432 mg, 4.00 mmol) in DMF (3 mL). After stifling the reaction overnight, the solvent was removed and the residue was directly purified by flash-column chromatography (dichloromethane/methanol 80:1-40:1).

The reaction yielded 86 mg (0.27 mmol, 67%) of 13b as a colorless oil: TLC: $R_f$=0.37 (DCM/MeOH 20:1); MS (MALDI-ToF, CHCA): m/z (%)=327.4 (100, [M+H]$^+$, calc. 327.2), 349.5 (5, [M+Na]$^+$, calc. 349.2); $^1$H-NMR (300 MHz, DMSO-D$_6$): δ=1.24-1.38 (m, 2H), 1.55-1.73 (m, 4H), 2.18-2.35 (m, 4H), 6.84-6.95 (m, 2H), 7.28-7.40 (m, 3H), 7.65 (m, 1H), 8.25 (m, 1H), 8.34 (m, 1H), 9.72 (s, 1H), 10.36 (s, 1H).

Compound 14b: $N^1$-(3-Methoxyphenyl)-$N^7$-phenyl-heptanediamide

A solution of 3-methoxyaniline (50 mg, 0.40 mmol) in DMF (3 mL) was added dropwise to a cooled solution of compound 3b (95 mg, 0.40 mmol), EDC.HCl (78 mg, 0.41 mmol), HOBt (64 mg, 0.40 mmol) and DIPEA (68 µl, 0.40 mmol) in DMF (5 mL). After stifling overnight, the solvent was removed in vacuo and the residue was triturated with ethylacetate/water (150 mL/20 mL). The phases were separated and the organic phase was washed two times with saturated NaCl solution, dried over $MgSO_4$ and evaporated. The residue was purified by column chromatography (dichloromethane/methanol 20:1).

The reaction yielded 84 mg (0.24 mmol, 62%) of 14b as a colorless oil: TLC: $R_f$=0.32 (DCM/MeOH 9:1); MS (MALDI-ToF, CHCA): m/z (%)=341.2 (60, $[M+H]^+$, calc. 341.2), 363.2 (70, $[M+Na]^+$, calc. 363.2); $^1$H-NMR (500 MHz, $CDCl_3$): δ=1.38-1.42 (m, 2H), 1.69-1.72 (m, 4H), 2.31-2.35 (m, 4H), 3.74 (s, 3H), 6.63 (m, 1H), 7.00 (m, 1H), 7.06 (m, 1H), 7.10 (m, 1H), 7.15 (m, 1H), 7.24-7.27 (m, 2H), 7.30-7.51 (m, 2H), 7.82-7.86 (m, 2H).

Compound 15b: $N^1$-(2,4-Dimethoxyphenyl)-$N^7$-phenylheptanediamide

A solution of 2,4-dimethoxyaniline (48 mg, 0.40 mmol) in DMF (3 mL) was added dropwise to a cooled solution of compound 3b (95 mg, 0.40 mmol), EDC.HCl (78 mg, 0.41 mmol), HOBt (64 mg, 0.40 mmol) and DIPEA (68 µl, 0.40 mmol) in DMF (5 mL). After stirring the reaction overnight, the reaction mixture was diluted with water until a colorless solid precipitated. The solid was collected by filtration, washed with water and recrystallised from water/acetonitrile.

The reaction yielded 97 mg (0.26 mmol, 65%) of 15b as a colorless oil: TLC: $R_f$=0.36 (DCM/MeOH 9:1); MS (MALDI-ToF, CHCA): m/z (%)=371.5 (100, $[M+H]^+$, calc. 371.2), 393.5 (50, $[M+Na]^+$, calc. 393.2); $^1$H-NMR (500 MHz, $CDCl_3$): δ=1.42-1.48 (m, 2H), 1.73-1.79 (m, 4H), 2.34-2.40 (m, 4H), 3.77 (s, 3H), 3.82 (s, 3H), 6.42-6.46 (m, 2H), 7.06 (m, 1H), 7.26-7.29 (m, 2H), 7.51-7.56 (m, 3H), 7.70 (m, 1H), 8.16 (m, 1H).

Compound 16b: $N^1,N^7$-Bis(2-aminophenyl)heptanediamide

A solution of 3b3 (140 mg, 0.40 mmol), EDC.HCl (78 mg, 0.41 mmol), HOBt (64 mg, 0.40 mmol) and DIPEA (68 µl, 0.40 mmol) in DMF (5 mL) was added drop-wise to a stirred and cooled solution of P1 (82 mg, 0.40 mmol) in DMF (3 mL). After stirring the reaction overnight, the solvent was removed and the residue was triturated with ethyl-acetate/water (150 mL, 2:1). The phases were separated and the organic phase was washed two times with 5% cold citric acid (20 mL), two times with sat. $NaHCO_3$ solution (20 mL), two times with saturated NaCl solution (40 mL), dried over $MgSO_4$ and evaporated. The residue was purified by flash-chromatography (DCM/MeOH 40:1).

The reaction yielded 186 mg (0.34 mg, 86%) of a colorless solid: TLC: $R_f$=0.21 (DCM/MeOH 20:1).

The Boc protecting groups were cleaved by adding a mixture of DCM/TFA (5 mL, 3:2) and stirring for 2 hours at room temperature. After the solvent was removed, the product was lyophilized. If necessary the product can be further purified by preparative HPLC.

This reaction yielded 185 mg (0.32 mmol, 80%) of a colorless solid: RP-HPLC: $R_t$=27.0 min; TLC: $R_f$=0.05 (DCM/MeOH 20:1); MS (MALDI-ToF, CHCA): m/z (%)=341.2 (100, $[M+H]^+$, calc. 341.2), 363.2 (20, $[M+Na]^+$, calc. 363.2); $^1$H-NMR (300 MHz, DMSO-$D_6$): δ=1.38-1.45 (m, 2H), 1.63-1.71 (m, 4H), 2.39-2.43 (m, 4H), 7.18-7.34 (m, 8H), 9.59-9.85 (br. s, 4H), 9.97 (s, 2H).

Compound 22a: $N^1$-Phenyl-$N^7$-phenylhexanediamide

A solution of aniline (37 mg, 0.40 mmol) in DMF (5 mL) was added drop-wise to a stirred solution of 3a (88 mg, 0.40 mmol), EDC.HCl (78 mg, 0.41 mmol), HOBt (64 mg, 0.40 mmol) and DIPEA (68 µL, 0.40 mmol) in DMF (5 mL). After stirring the reaction overnight, water was added until a colorless solid precipitated. The crude product was collected by filtration and recrystallized from water/ethanol.

This reaction yielded 64 mg (0.21 mmol, 54%) of 22a as a colorless solid: TLC: $R_f$=0.35 (DCM/MeOH 20:1); MS (MALDI-ToF, CHCA): m/z (%)=297.4 (80, $[M+H]^+$, calc. 297.2), 319.4 (20, $[M+Na]^+$, calc. 319.2); $^1$H-NMR (300 MHz, DMSO-$D_6$): δ=1.60-1.67 (m, 4H), 2.33-2.41 (m, 4H), 6.99-7.03 (m, $^3J$=7.0 Hz, 2H), 7.26-7.30 (m, $^3J$=7.6 Hz, 4H), 7.58-7.60 (m, $^3J$=7.6 Hz, 4H), 9.88 (s, 2H).

Synthesis of Additional Precursors

Compound P2: tert-Butyl-4-aminophenylcarbamate

A solution of di-tert-butyldicarbonate (2.0 g, 10 mmol) in DMF (25 mL) was added dropwise to stirred solution of 1,4-phenylenediamine (1.08 g, 10 mmol) in 50 mL DMF at 55° C. After the addition the reaction mixture was stirred for 2 hours. The solvent was removed in vacuo and the residue was taken up in ethylacetate (150 mL). The organic phase was washed three times with 5% citric acid, three times with saturated sodium-bicarbonate and three times with saturated NaCl solution (40 mL). The organic phase was then dried over $MgSO_4$ and evaporated. The residue was recrystallised from ethylacetate.

This reaction yielded 1.35 g (6.50 mmol, 65%) of P2 as a colorless solid: TLC: $R_f$=0.39 (DCM/MeOH 20:1); $^1$H-NMR (500 MHz, $CDCl_3$): δ 1.50 (s, 9H), 3.50 (br. s, 2H), 6.33 (br. s, 1H), 6.60-6.64 (AA'BB', 2H), 7.11-7.13 (AA'BB', 2H). $^{13}$C-NMR (128 MHz, $CDCl_3$): δ 28.4, 80.0, 115.6, 116.7, 120.9, 129.7, 153.3.

Compound P3: 7-(4-(tert-Butoxycarbonylamino) phenylamino)-7-oxoheptanoic acid

Pimelic acid (200 mg, 1.25 mmol) was refluxed in 10 mL acetic anhydride for 30 minutes. The solvent was removed to complete dryness. The residue was diluted in 5 mL dry THF, then P2 (208 mg, 1.00 mmol) in 5 mL dry THF was added dropwise. The reaction was stirred overnight and then the solvent was evaporated. The residue was taken up in 100 mL ethylacetate and then washed two times with 50 mL with water and two times with saturated NaCl. After drying over $MgSO_4$ the solvent was evaporated. The crude residue was purified by flashcolumn chromatography on silica gel (DCM/MeOH 40:1).

This reaction yielded 140 mg (0.4 mmol, 40%) of P3 as a colorless solid: TLC: $R_f$=0.14 (DCM/MeOH 20:1); MS (MALDI-ToF, CHCA): m/z (%)=351.3 (15, [M+H]$^+$, calc. 351.2), 373.4 (100, [M+Na]$^+$, calc. 373.2); $^1$H-NMR (500 MHz, D$_6$-DMSO): δ1.24-1.29 (m, 4H), 1.45 (s, 9H), 1.47-1.53 (m, 4H), 2.21-2.26 (m, 2H), 7.33 (AA'BB', 2H), 7.44 (AA'BB', 2H), 9.20 (s, 1H), 9.70 (s, 1H).

Compound 80b:
7-Oxo-7-(2-methoxyphenylamino)heptanoic acid

A solution of pimelic acid (5.00 g, 31.2 mmol) in acetic anhydride (10 mL) was heated under reflux for 1 hour. After cooling to room temperature, the solvent was removed in vacuo. The crude yellow oil was used without any further purification for the next step. o-Anisidine (2.10 mL, 28.7 mmol) was added to a stirred solution of the produced anhydride in anhydrous THF (10 mL). After stirring at r.t. for 30 min, the reaction mixture was diluted with water until a colorless solid precipitated, which was collected by filtration. Recrystallisation from water/acetonitrile gave the pure compound as a colorless solid.

This reaction yielded 1.86 g (7.02 mmol, 25%) of 80b as a colorless solid: TLC: R$_f$=0.21 (DCM/MeOH 20:1); MS (MALDI-ToF, CHCA): m/z (%)=266.3 (100, [M+H]$^+$, calc. 266.1), 288.4 (24, [M+Na]$^+$, calc. 288.1); $^1$H-NMR (500 MHz, D$_4$-MeOH): δ 1.31-1.36 (m, 2H), 1.58-1.64 (m, 4H), 2.28-2.41 (m, 4H), 3.86 (s, 3H), 6.91-7.02 (m, 1H), 7.07-7.12 (m, 2H), 7.94 (m, 1H).

Compound 100b: 7-Oxo-7-(o-tolylamino)heptanoic acid

A solution of pimelic acid (2.50 g, 16.4 mmol) in acetic anhydride (10 mL) was heated under reflux for 20 minutes. After cooling to room temperature, the solvent was removed in vacuo. The crude yellow oil was used without any further purification for the next step. o-Toluidine (1.77 mL, 16.0 mmol) was added to a stirred solution of the produced anhydride in anhydrous THF (10 mL). After stifling at room temperature for 1 hour, the reaction mixture was diluted with water until a colorless solid precipitated, which was collected by filtration. Recrystallisation from water/ethanol gave the pure compound as a colorless solid.

This reaction yielded 1.26 g (5.1 mmol, 31%) of 100b as a colorless solid: TLC: R$_f$=0.16 (DCM/MeOH 20:1); MS (MALDI-ToF, CHCA): m/z (%)=250.3 (73, [M+H]$^+$, calc. 250.1), 272.4 (56, [M+Na]$^+$, calc. 272.1); $^1$H-NMR (500 MHz, D$_4$-MeOH): δ 1.41-1.49 (m, 2H), 1.64-1.81 (m, 4H), 2.23 (s, 3H) 2.30 (d, $^3$J=7.6 Hz, 2H), 2.41 (d, $^3$J=7.6 Hz, 2H), 3.32 (s, 3H), 7.01-7.18 (m, 2H), 7.21-7.23 (m, 1H), 7.25-7.29 (m, 1H).

Compound 101b: 7-Oxo-7-(p-tolylamino)heptanoic acid

The synthesis method was the same as that for 100b, with the exception that p-toluidine was used in place of o-toluidine.

This reaction yielded 1.56 g (6.3 mmol, 38%) of 101b as a colorless solid: TLC: R$_f$=0.17 (DCM/MeOH 20:1); MS (MALDI-ToF, CHCA): m/z (%)=250.3 (100, [M+H]$^+$, calc. 250.1), 272.4 (24, [M+Na]$^+$, calc. 272.1); $^1$H-NMR (500 MHz, D$_4$-MeOH): δ 1.42-1.50 (m, 2H), 1.63-1.79 (m, 4H), 2.35 (s, 3H) 2.31 (d, $^3$J=7.5 Hz, 2H), 2.43 (d, $^3$J=7.6 Hz, 2H), 3.32 (s, 3H), 7.09-7.12 (AA'BB', 2H), 7.48-7.51 (AA'BB', 2H).

Synthesis of Additional Inhibitors

TABLE 3

Additional Inhibitors

| Number | Structure | Mol. Wt. | Formula |
|---|---|---|---|
| 81b | 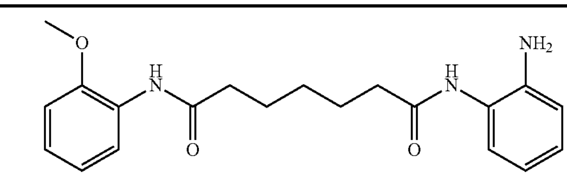 | 355.43 g/mol | C$_{20}$H$_{25}$N$_3$O$_3$ |
| 82b | 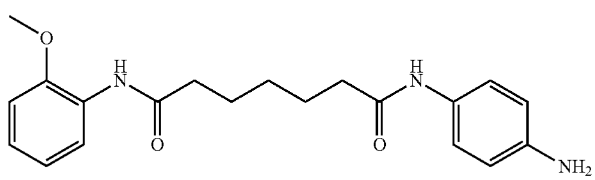 [SMILES: COc1ccccc1NC(=O)CCCCCC(=O)Nc1ccc(N)cc1] | 355.43 g/mol | C$_{20}$H$_{25}$N$_3$O$_3$ |
| 102b | 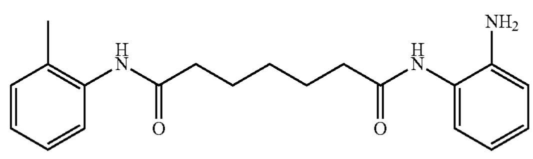 [SMILES: Cc1ccccc1NC(=O)CCCCCC(=O)Nc1ccccc1N] | 339.43 g/mol | C$_{20}$H$_{25}$N$_3$O$_2$ |
| 106b | 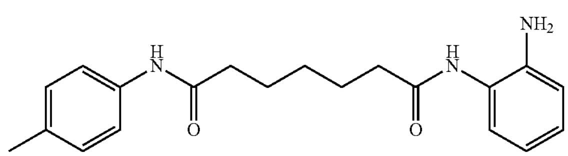 [SMILES: Cc1ccc(NC(=O)CCCCCC(=O)Nc2ccccc2N)cc1] | 339.43 g/mol | C$_{20}$H$_{25}$N$_3$O$_2$ |

Compound 81b: N¹-(2-aminophenyl)-N⁷-(2-methoxyphenyl)heptanediamide

A solution of 80b (1.86 g, 7.00 mmol), EDC.HCl (1.33 g, 7.00 mmol), HOBt (1.071 g, 7.00 mmol) in DMF (10 mL) was added dropwise to a stirred and cooled solution of 1,2-phenylenediamine (1.50 g, 14.0 mmol) in DMF (10 mL). After stifling the reaction for 1 hour at room temperature, the solvent was removed and the residue was taken up in 150 mL ethylacetate and washed with two times with 20 mL 5% citric acid, two times with 20 mL saturated sodium bicarbonate and two times with saturated NaCl. After drying over $MgSO_4$ the solvent was evaporated and the crude product was recrystallized from water/ethanol.

The reaction yielded 1.366 g (3.85 mmol, 55%) of 81b as a yellow solid: TLC: $R_f$=0.53 (DCM/MeOH 20:1); MS (MALDI-ToF, CHCA): m/z (%)=356.0 (100, [M+H]⁺, calc. 356.2), 378.0 (20, [M+Na]⁺, calc. 378.2); ¹H-NMR (500 MHz, $D_4$-MeOH): δ 1.46-1.53 (m, 2H), 1.71-1.80 (m, 4H), 2.41-2.47 (m, 4H), 3.85 (s, 3H), 6.67-6.72 (m, 1H), 6.82-6.92 (m, 2H), 6.97-7.02 (m, 2H), 7.03-7.10 (m, 2H), 7.90 (m, 1H).

Compound 82b: N¹-(4-aminophenyl)-N⁷-(2-methoxyphenyl)heptanediamide

A solution of 2-methoxyaniline (33 μL, 286 μmol) in DMF (5 mL) was added dropwise to a cooled solution of P3 (100 mg, 286 μmol), EDC.HCl (55 mg, 286 μmol), HOBt (44 mg, 286 μmol) in DMF (5 mL). After stifling for 3 hours, the solvent was removed in vacuo, and the residue was triturated with 10 mL DCM/TFA (1:1) and stirred for 2 hours at room temperature. The solvent was removed and the residue was recrystallized from acetonitrile/water.

The reaction yielded 55 mg (154 μmol, 54%) of 82b as a colorless solid: TLC: $R_f$=0.26 (DCM/MeOH 20:1); RP-HPLC: $R_t$=28 min; MS (MALDI-ToF, CHCA): m/z (%)=356.3 (100, [M+H]⁺, calc. 356.2), 378.2 (28, [M+Na]⁺, calc. 378.2); ¹H-NMR (500 MHz, $D_6$-DMSO): δ 1.30-1.35 (m, 2H), 158-1.64 (m, 4H), 2.29-2.39 (m, 4H), 3.80 (s, 3H), 6.85-6.88 (m, 1H), 7.00-7.06 (m, 2H), 7.14 (AA'BB', 2H), 7.62 (AA'BB', 2H), 7.90 (m, 1H), 9.00 (s, 1H), 9.97 (s, 1H).

Compound 102b: N¹-(2-aminophenyl)-N⁷-o-tolyl-heptanediamide

A solution of 100b (200 mg, 0.79 mmol), EDC.HCl (152 mg, 0.79 mmol), HOBt (121 mg, 0.79 mmol) in DMF (5 mL) was added dropwise to a stirred and cooled solution of 1,2-phenylenediamine (430 mg, 4.00 mmol) in DMF (5 mL). After stifling the reaction for 1 hour at room temperature, water was added until a white solid precipitated, which was collected by filtration and recrystallized from ethanol/water.

This reaction yielded 186 g (0.55 mmol, 69%) of 102b as a colorless solid: TLC: $R_f$=0.21 (DCM/MeOH 20:1); MS (MALDI-ToF, CHCA): m/z (%)=340.4 (95, [M+H]⁺, calc. 340.2), 362.4 (43, [M+Na]⁺, calc. 362.2); ¹H-NMR (500 MHz, $D_6$-DMSO): δ 1.37-1.42 (m, 2H), 1.59-1.65 (m, 4H), 2.32-2.36 (m, 4H), 3.32 (s, 3H), 4.80 (br. s, 2H), 6.49-6.55 (m, 1H), 6.70-6.72 (m, 1H), 6.87-6.89 (m, 1H), 7.06-7.19 (m, 4H), 7.35-7.37 (m, 1H), 9.08 (s, 1H), 9.22 (s, 1H).

Compound 106b: N¹-(2-aminophenyl)-N⁷-p-tolyl-heptanediamide

A solution of 101b (750 mg, 3.00 mmol), EDC.HCl (573 mg, 3.00 mmol), HOBt (460 mg, 3.00 mmol) in DMF (20 mL) was added dropwise to a stirred and cooled solution of 1,2-phenylenediamine (1.62 mg, 15.0 mmol) in DMF (10 mL). After stifling the reaction for 2 hours at room temperature, water was added until a white solid precipitated, which was collected by filtration and recrystallized from ethanol/water.

This reaction yielded 742 mg (2.19 mmol, 73%) of 101b as a colorless solid: TLC: $R_f$=0.53 (DCM/MeOH 20:1); MS (MALDI-ToF, CHCA): m/z (%)=340.3 (100, [M+H]⁺, calc. 340.2), 362.4 (24, [M+Na]⁺, calc. 362.2); ¹H-NMR (500 MHz, $D_6$-DMSO): δ 1.33-1.36 (m, 2H), 1.60-1.65 (m, 4H), 2.25-2.33 (m, 4H), 3.35 (s, 3H), 4.80 (br. s, 2H), 6.50-6.54 (m, 1H), 6.70-6.72 (m, 1H), 6.87-6.90 (m, 1H), 7.07-7.09 (AA'BB', 2H), 7.13-7.16 (m, 1H), 7.45-7.47 (AA'BB', 2H), 9.05 (s, 1H), 9.76 (s, 1H).

Example 3—Histone Compositions of Active & Repressed Frataxin Alleles

Figure 1B:
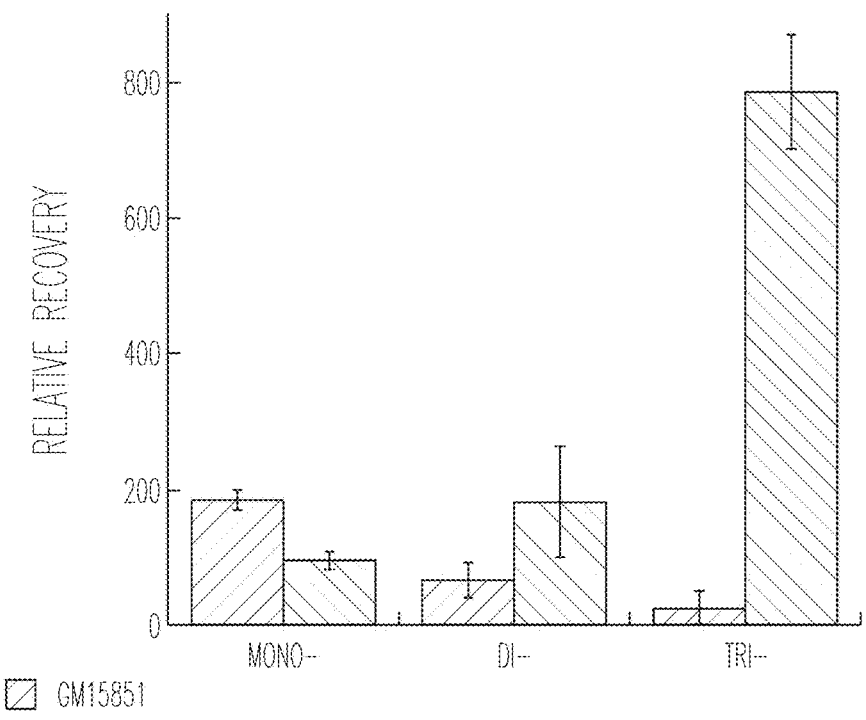

To assess whether histone modifications play a role in gene silencing in FRDA, the histone acetylation state of the frataxin gene in an Epstein Barr virus transformed lymphoid cell line derived from an FRDA patient (line GM15850, alleles with 650 and 1030 GAA.TTC repeats in the frataxin gene, from the NIGMS Human Genetic Cell Repository, Coriell Institute, Camden, N.J.) was monitored by chromatin immunoprecipitation (ChIP) with antibodies to the acetylated forms of histones H3 and H4. For comparison, we used a similar cell line from a normal sibling of this patient (line GM15851, normal range of repeats). As expected, the cell line from the FRDA patient has a markedly lower level (13±6%, range of 20 determinations (Burnett et al. P.N.A.S. 103: 11497-502 (2006)) of frataxin mRNA compared to the cell line from the unaffected sibling, as determined by quantitative real time/reverse transcriptase PCR (qRT-PCR, see below). Primers that interrogate the chromatin regions upstream or downstream of the GAA.TTC repeats in the first intron of the frataxin gene, as well as the promoter element, were used in the ChIP experiments, with the levels of immunoprecipitated DNA quantified by real-time PCR (FIG. 1A). There was no difference in the expression of glyceraldehyde-3-phosphodehydrogenase (GAPDH) mRNA between the two cell lines, and GAPDH was used as a recovery standard in the ChIP experiments. The coding region of active frataxin alleles in the GM15851 cell line is enriched in histones acetylated at H3-K9, H3-K14, H4-K5, H4-K8, H4-K12, and H4-K16, compared to the inactive alleles in the GM15850 FRDA cell line, which are clearly depleted in these histone modifications. No significant differences in the levels of histone acetylation were found on the frataxin promoter in the two cell lines. Additionally, we examined the methylation status of H3-K9 with antibodies to mono-, di- and tri-methylated H3-K9, and H3-K9 is highly trimethylated in the FRDA cell line compared to the normal cell line (FIG. 1B). Along with hypoacetylation, trimethylation of H3-K9 is a hallmark of heterochromatin (Elgin & Grewal, Curr. Biol. 13:R895-8 (2003)). Thus, the histone postsynthetic modification states within the coding region of inactive frataxin alleles are consistent with a chromatin-mediated mechanism as the cause of gene silencing in FRDA (Saveliev et al. Nature 422:909-13 (2003)).

Example 4—Effect of Histone Deacetylase Inhibitors on Frataxin Gene Expression To further assess the possibility that gene silencing at expanded GAA.TTC frataxin alleles is due to histone deacetylation and heterochromatin formation, the effects of a series of commercial HDAC inhibitors on the levels of histone acetylation and frataxin transcription in the FRDA and normal lymphoid cell lines were monitored using antibodies to the acetylated forms of histones H3 and H4. The inhibitors tested included the hydoxamic acids trichostatin A, suberoyl bis-hydroxamic acid (SBHA), and suberoylanilide hydroxamic acid (SAHA); the benzamide-type SAHA derivative BML-210 (Wong et al. *J. Am. Chem. Soc.* 125:5586-7 (2003)); and the small caboxylate valproic acid. The structures of SAHA, PAOA (compound 4b), and SAOA (compound 4c, BML-210) are illustrated below:

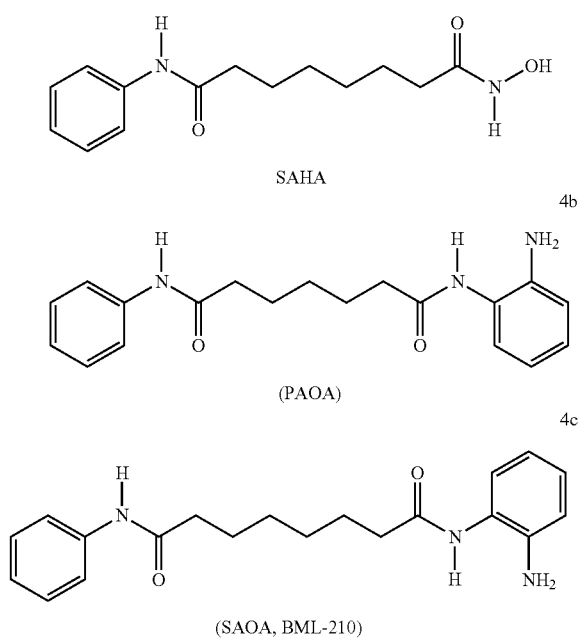

Figure 2A:
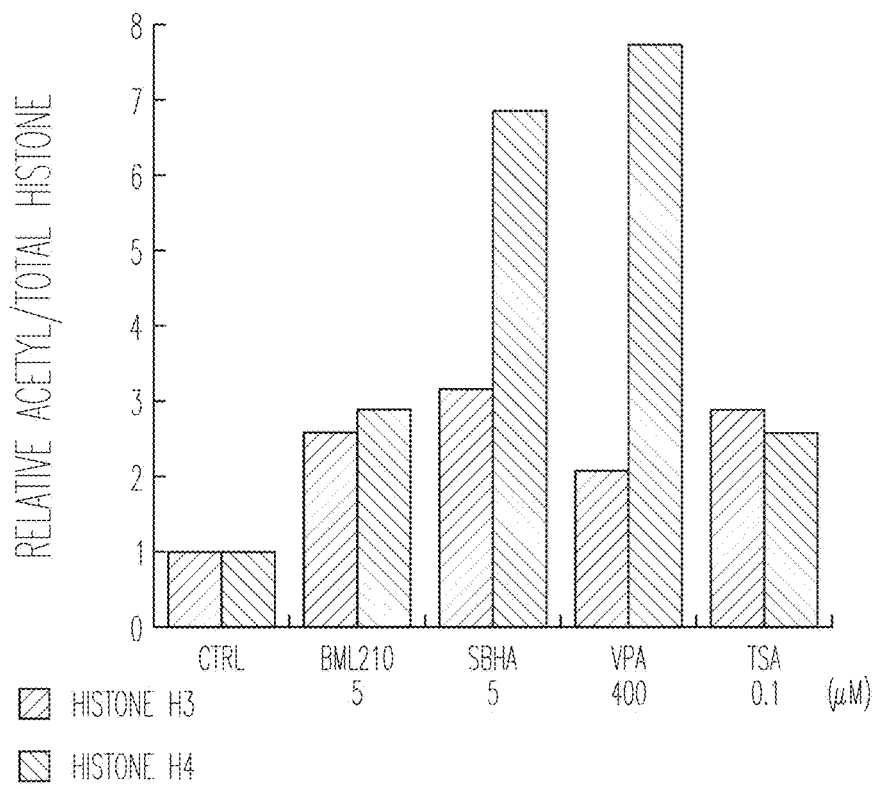
FIG. 2A-2B show bar graphs illustrating the effects of histone deacetylase inhibitors on acetylation and frataxin mRNA in FRDA cells.
Figure 2B:
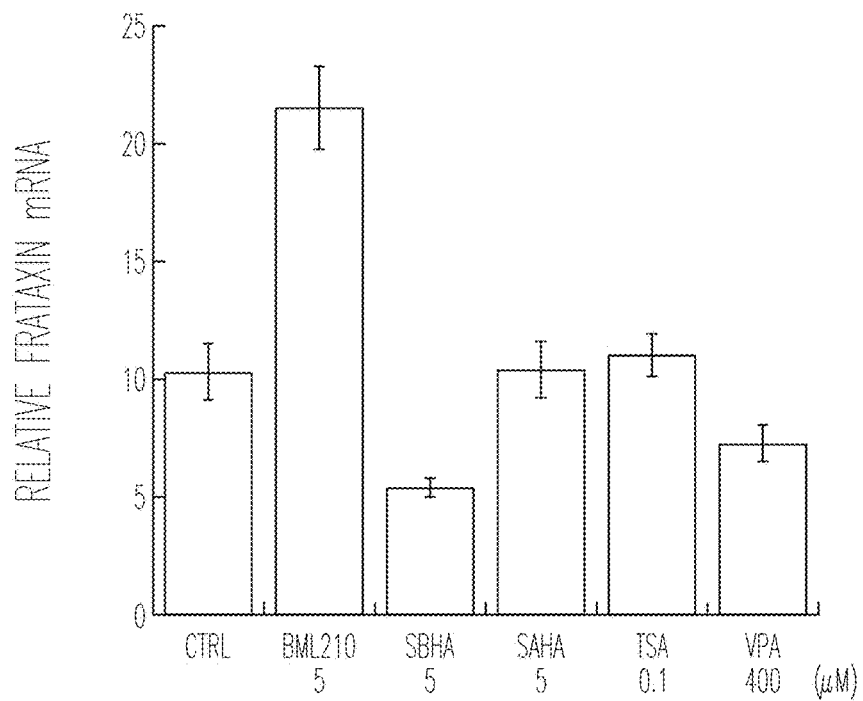

Results in FIG. 2A indicate that all of the HDAC inhibitors increased the levels of total acetylated histones in the FRDA cell line when used at their reported $IC_{50}$ value for HDAC inhibition. Cyclic peptide inhibitors were also tested, but were found to be highly cytotoxic to the lymphoid cells, and thus not pursued. Each of the HDAC inhibitors was also tested for effects on frataxin mRNA levels in the FRDA cell line by qRT-PCR (at the $IC_{50}$ values), and only BML-210 increased the level of frataxin mRNA ~2-fold (FIG. 2B). The levels of GAPDH mRNA were not changed by the HDAC inhibitors and were used for normalization in all qRT-PCR experiments. Over the concentration range necessary for HDAC inhibition (1 to 5 μM), BML-210 is not cytotoxic to the lymphoid cell lines (determined by trypan blue exclusion) and does not markedly affect cell growth rates. The structurally related compound SAHA had no effect on frataxin transcription and SBHA had a negative effect (50% decrease), even though both compounds were more effective HDAC inhibitors than BML-210 (FIG. 2A).

Example 5—Evaluation of HDAC Inhibitors

To optimize the activity of BML-210, compound 4c ($N^1$-(2-aminophenyl)-$N^8$-phenyloctanediamide, Wong et al. *J. Am. Chem. Soc.* 125:5586-7 (2003)) and a series of related analogues (see Table 4) were synthesized by a facile two-step protocol (see Example 2). Derivatives were designed to explore the length of the linker region between the two ring systems (four, five and six methylenes), the nature of the rings (phenyl, pyridine, quinoline), and the type and position of ring substituents (methyl and methoxy groups, etc., Table 4).

TABLE 4

Relative Activities of Histone Deacetylase Inhibitors

| Compound | | Fold-change[1] ($IC_{50}$)[2] |
|---|---|---|
| 4a | 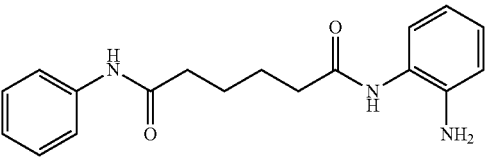 [SMILES: Nc1ccccc1NC(=O)CCCCC(=O)Nc1ccccc1] | 1.4 ± 0.06 (238 μM) |
| 4b | 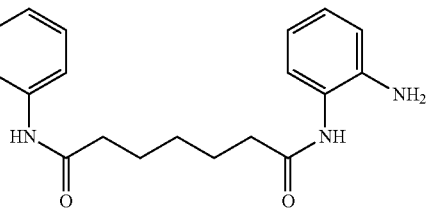 | 2.5 ± 0.24 (78 μM) |

TABLE 4-continued
Relative Activities of Histone Deacetylase Inhibitors
| | Compound | Fold-Change (IC$_{50}$) |
|---|---|---|
| 4c | 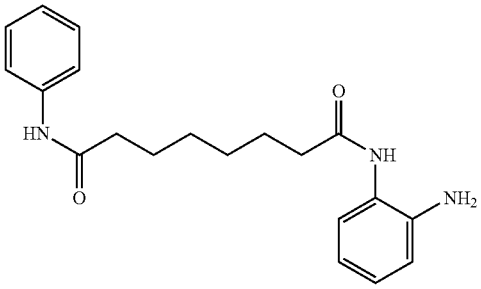 [SMILES: Nc1ccccc1NC(=O)CCCCCCC(=O)Nc1ccccc1] | 1.4 ± 0.06 (87 μM) |
| 5b | 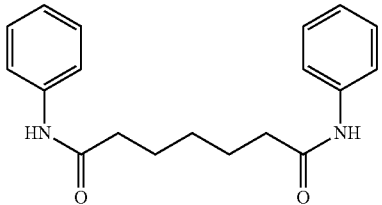 [SMILES: O=C(CCCCCC(=O)Nc1ccccc1)Nc1ccccc1] | 1.4 ± 0.15 (204 μM) |
| 6b | 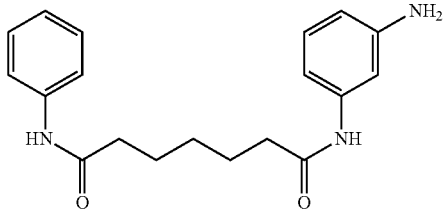 [SMILES: Nc1cccc(NC(=O)CCCCCC(=O)Nc2ccccc2)c1] | 1.5 ± 0.13 (500 μM) |
| 6c | 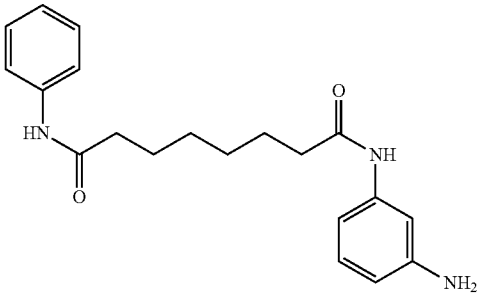 [SMILES: Nc1cccc(NC(=O)CCCCCCC(=O)Nc2ccccc2)c1] | 2.1 ± 0.15 (85 μM) |
| | Compound | Fold-Change (IC$_{50}$) |
|---|---|---|
| 7b | 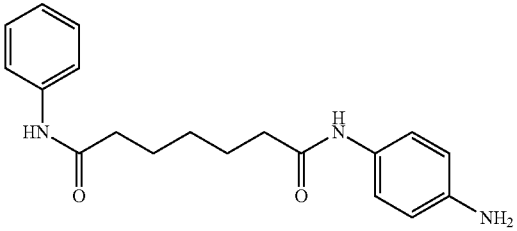 [SMILES: Nc1ccc(NC(=O)CCCCCC(=O)Nc2ccccc2)cc1] | 2.6 ± 0.14 (123 μM) |
| 7c | 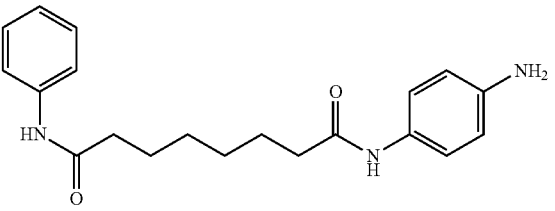 [SMILES: Nc1ccc(NC(=O)CCCCCCC(=O)Nc2ccccc2)cc1] | 2.0 ± 0.08 (186 μM) |

TABLE 4-continued

Relative Activities of Histone Deacetylase Inhibitors

| | | |
|---|---|---|
| 8b | [structure: PhNH-CO-(CH2)4-CO-NH-(2-pyridyl)] | 2.6 ± 0.14 (140 μM) |
| 8c | [structure: PhNH-CO-(CH2)5-CO-NH-(2-pyridyl)] | 2.0 ± 0.08 (99 μM) |
| 9b | [structure: PhNH-CO-(CH2)4-CO-NH-(2-methoxyphenyl)] | 2.3 ± 0.11 (54 μM) |
| 9c | [structure: PhNH-CO-(CH2)5-CO-NH-(2-methoxyphenyl)] | 1.8 ± 0.07 (470 μM) |
| 10b | [structure: PhNH-CO-(CH2)4-CO-NH-(4-methoxyphenyl)] | 2.5 ± 0.17 (438 μM) |
| 11b | [structure: PhNH-CO-(CH2)4-CO-NH-(8-quinolyl)] | 3.0 ± 0.17 (17 μM) |
| 12b | [structure: PhNH-CO-(CH2)4-CO-NH-(3-quinolyl)] | 2.5 ± 0.17 (84 μM) |
| 13b | [structure: (2-pyridyl)-NH-CO-(CH2)4-CO-NH-(2-aminophenyl)] | 2.4 ± 0.10 (91 μM) |

TABLE 4-continued

Relative Activities of Histone Deacetylase Inhibitors

| | | |
|---|---|---|
| 14b | 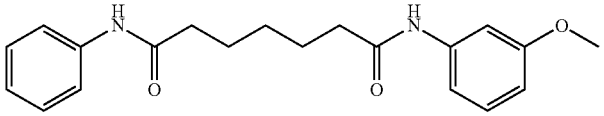 | 1.8 ± 0.12 (>1 mM) |
| 15b | 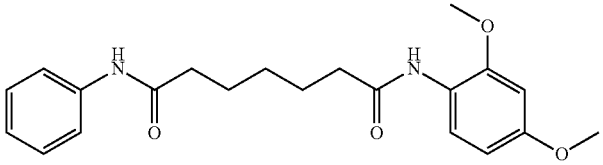 [SMILES: COc1ccc(NC(=O)CCCCCC(=O)Nc2ccccc2)c(OC)c1] | 1.5 ± 0.06 (387 µM) |
| 16b | 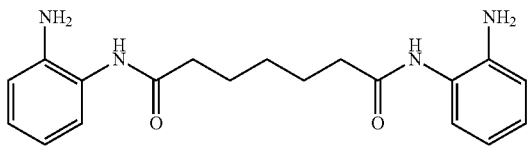 [SMILES: Nc1ccccc1NC(=O)CCCCCC(=O)Nc1ccccc1N] | 3.1 ± 0.19 (14 µM) |

[1]Fold-change of frataxin mRNA in affected GM15850 cells, normalized to GAPDH mRNA, were determined in triplicate by real-time quantitative RT-PCR after incubation with each compound at 5 µM for 96 h. Values are relative to untreated control cells.
[2]IC$_{50}$ values (in parenthesis below fold-change values) were determined by total histone deacetylation inhibition in a HeLa nuclear extract.

The compounds were tested for their effects on frataxin mRNA levels in the FRDA cell line by qRT-PCR and for their activity as HDAC inhibitors in a HeLa nuclear extract (Table 4). The IC$_{50}$ values, representing the general HDAC inhibitory activities of these compounds, range from 14 µM (compound 16b) to >1000 µM (compound 14b, Table 4). The same IC$_{50}$ values were obtained with an extract from FRDA lymphoid cells for several of the compounds (not shown). For activation of transcription, each of the compounds was tested at a concentration of 5 µM in culture medium for 96 hours. Importantly, and in contrast to the common HDAC inhibitors such as SAHA and TSA, none of the compounds affected the viability of the lymphoid cell lines (at concentrations required for transcriptional activation). Compounds with six (4c and derivatives) or four (4a) methylene groups in the linker region are less potent transcriptional activators than the corresponding pimeloylanilide derivatives (4b, N$^1$-(2-aminophenyl)-N$^7$-phenyl-heptanediamide (Wong et al. J. Am. Chem. Soc. 125:5586-7 (2003)), and derivatives, Table 4), and amino- or methoxy-substitutions at the ortho- and para-positions are most effective in increasing levels of frataxin mRNA. The quinoline derivatives of pimeloylanilide are also highly active (compounds 11b and 12b). The symmetric diamino compound 16b, N$^1$,N$^7$-bis(2-aminophenyl) heptanediamide, is the most effective compound in the FRDA cell line (3.1-fold increase in frataxin mRNA at 5 µM and 3.5-fold increase at 10 µM). 16b exhibits an IC$_{50}$ value of 14 µM in a HeLa nuclear extract HDAC inhibition assay, compared to an IC$_{50}$ of 87 µM for 4c and 78 µM for 4b. There is no apparent correlation between total HDAC inhibition activity and the ability of the compounds to activate transcription of the frataxin gene in live cells. These findings are in accord with the observation that common class I and II HDAC inhibitors have no effect on frataxin transcription (FIG. 2B). Since the nuclear extracts contain several HDAC enzymes, in many different multi-protein complexes, the standard HDAC inhibition assay only provides an overall measure of inhibitory activity for the sum of all these enzymatic activities. We interpret these results to indicate that the general HDAC assay does not reflect the IC$_{50}$ for the true target enzyme involved in silencing the frataxin gene.

Example 6—HDAC Inhibitors Increase Frataxin Protein Levels

Figure 3:
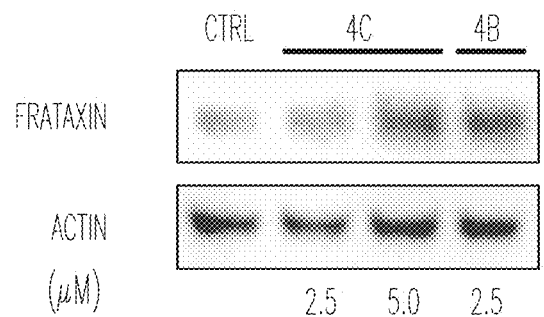
FIG. 3 is an autoradiogram showing that HDAC inhibitors increase frataxin protein in the FRDA lymphoid cell line. Cells were incubated with the indicated concentrations of HDAC inhibitors for 4 days prior to western blot analysis with antibody to human frataxin or actin. Equivalent amounts of total cell extract protein were loaded in each lane. The fold changes in frataxin protein compared to untreated control cells (denoted "Ctrl" in the figure), normalized to the actin signals, are 1.6 (2.5 µM 4c/BML-210), 3.4 (5 µM 4c), and 3.5 (2.5 µM 4b).

Since the primary transcripts of pathogenic frataxin alleles contain long GAA repeat RNA sequences, it is conceivable that these RNAs may not be correctly processed and increases in frataxin protein may not be observed on treatment with HDAC inhibitors. To test whether the HDAC inhibitors lead to increased levels of frataxin protein in treated lymphoid cells, total cellular proteins were subjected to SDS-PAGE and western blotting with anti-frataxin or anti-actin antibodies (FIG. 3). A ~3-fold increase in frataxin protein is observed with 4c (BML-210) at 5 µM, and a similar increase in frataxin protein was observed with 4b at 2.5 µM in the FRDA cells. These increases in frataxin protein equal or exceed the observed increases in frataxin mRNA in cultured cells (Table 4).

Figure 4A:
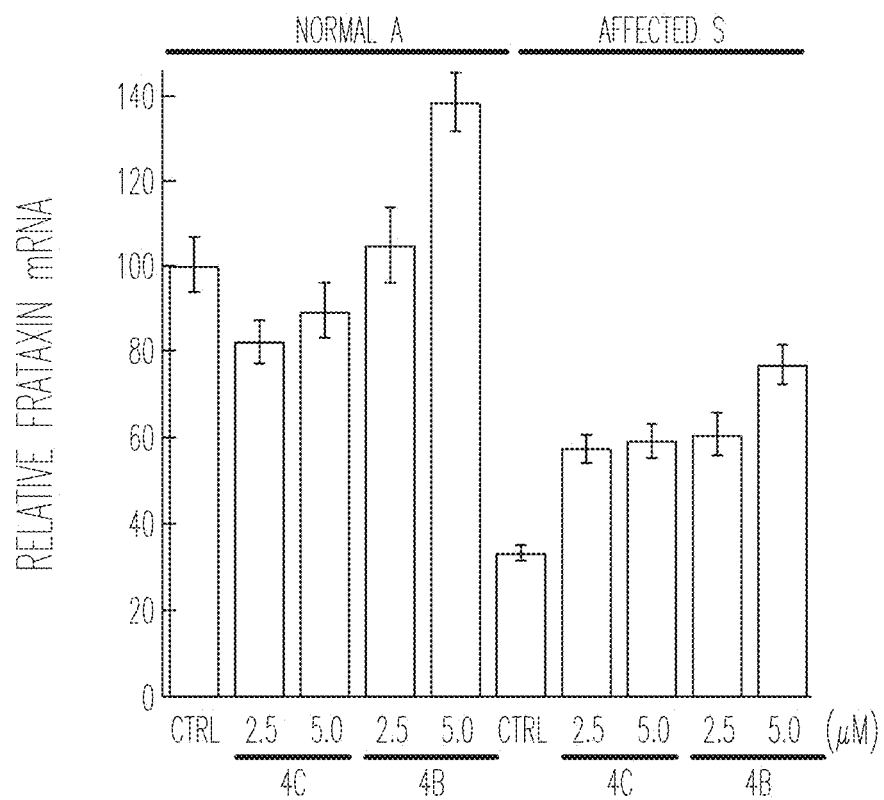
FIG. 4A-4C show bar graphs showing that HDAC inhibitors increase frataxin mRNA in primary lymphocytes from FRDA patients. Frataxin mRNA levels were determined by qRT-PCR, relative to that of GAPDH, in lymphocytes from an unaffected individual A (normal range of repeats) and his/her FRDA sibling (affected S, with frataxin alleles containing and 906 and 88 GAA repeats) (FIG. 4A); in lymphocytes from carrier C and affected AC (801 and 597 repeats) (FIG. 4B); and in lymphocytes from carrier D, and affected J (550 and 530 repeats) and M (1030 and 650 repeats) (FIG. 4C). The indicated concentrations of HDAC inhibitors were included in the cell culture medium, and frataxin and GAPDH mRNA levels were determined at 48 hours. Data are normalized to the frataxin mRNA level found in lymphocytes from the unaffected individuals (normal in FIG. 4A or carriers in FIGS. 4B and 4C, =100%). The means and standard deviations for three independent determinations are shown.

Example 7—HDAC Inhibitors Increase Frataxin mRNA in Primary Lymphocytes from FRDA Patients Frataxin protein deficiency in the human disease affects non-proliferating cell types (neuronal cells and cardiomyocytes). While these human cells are not readily available for experimentation, primary lymphocytes can be obtained from donor blood, and lymphocytes that are not treated with cytokines do not divide in culture under the conditions of our experiments. We thus tested the effect of HDAC inhibitors on frataxin mRNA levels in primary lymphocytes obtained from FRDA patients and carrier or normal relatives of these patients (under an approved Human Subjects Protocol, with appropriate informed consent). Lymphocytes were isolated by Ficoll gradient centrifugation, and cells were incubated in culture for 16 h prior to the addition of 2.5 or 5 µM 4b or 4c to the culture medium; cells were harvested and RNA purified after an additional 48 hours in culture. Similar to the established cell lines, the HDAC inhibitors did not affect viability of primary lymphocytes over this time period. Lymphocytes from affected individual S had 33±2% of the level of frataxin mRNA compared to lymphocytes from his/her homozygous normal sibling A (FIG. 4A). Neither compound affected the levels of GAPDH mRNA in cells from either individual, while incubation for two days in culture with 4b and 4c markedly stimulated frataxin mRNA synthesis in lymphocytes from the affected individual (FIG. 4A). The relative levels of frataxin mRNA increased by 1.8-fold (80% increase) with 5 µM 4c, and by 2.3-fold (130% increase) with 5 µM 4b in FRDA lymphocytes. 4b had a smaller effect (38% increase) in lymphocytes from the unaffected sibling, while 4c had no positive effect on frataxin mRNA in these cells. Importantly, 4b increased the frataxin mRNA level in lymphocytes from the affected individual to ~80% of that in lymphocytes from the unaffected individual.

Figure 4B:
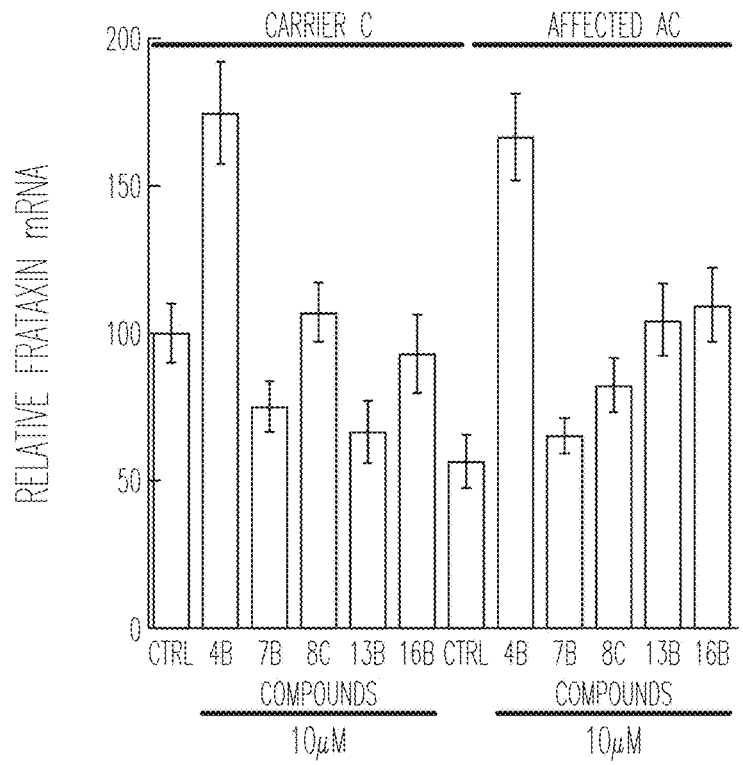
Figure 4C:
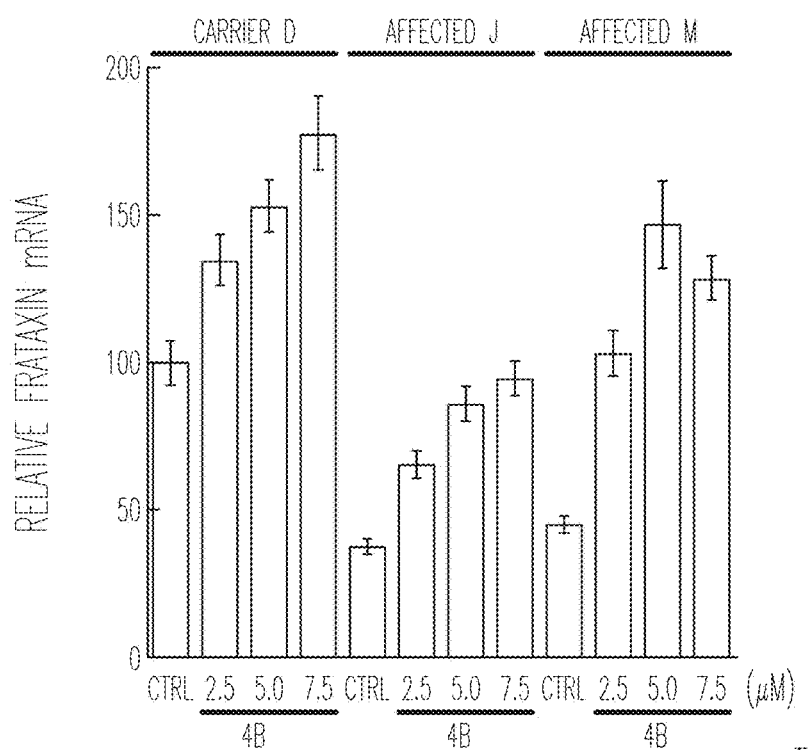

We next compared the transcriptional activities of five of the most active HDAC inhibitors identified in the established cell line in primary lymphocytes from a heterozygous carrier (subject C, frataxin mRNA normalized to 100%) and FRDA patient AC (FIG. 4B). Again, 4b was highly active in increasing frataxin mRNA levels in cells obtained from carrier C and affected AC, bringing the frataxin mRNA level in the FRDA lymphocytes to ~160% of that found in the untreated carrier lymphocytes. Compounds 13b and 16b were also active and brought the frataxin mRNA level in the FRDA lymphocytes to that found in lymphocytes from the unaffected carrier. Unlike the established FRDA cell line (Table 4), compounds 7b and 8c were relatively inactive in primary lymphocytes. Also in contrast to results with the established cell line where 16b is most active, 4b was found to be the most active compound in primary lymphocytes, and we thus pursued 4b in subsequent studies. We next tested the effects of increasing concentrations of 4b on frataxin mRNA levels in lymphocytes from two sibling FRDA patients J and M, and carrier relative D (with frataxin mRNA levels normalized to 100% in the carrier lymphocytes, FIG. 4C). 4b increased the levels of frataxin mRNA in each of the tested lymphocyte populations, and the level of frataxin mRNA in the FRDA patient lymphocytes was increased to at least that of the carrier. Notably, frataxin mRNA was nearly doubled in the carrier, suggesting that the inactive frataxin allele has been nearly completely re-activated. While differences in the fold-increases in frataxin mRNA are observed with 4b in primary lymphocytes from different donors (compare FIGS. 4A-C), this compound consistently increases frataxin mRNA in FRDA and carrier lymphocytes obtained from 12 out of 12 families, and in each instance the frataxin mRNA level in the FRDA lymphocytes is increased to approximately that of untreated lymphocytes from a carrier relative. We have thus obtained a level of gene activation that represents a therapeutically useful increase in frataxin mRNA. We note that the HDAC inhibitors are more effective in primary lymphocytes than in the FRDA cell line, and this difference may be related to the more severe silencing of the frataxin gene observed in the FRDA cell line.

Example 8—HDAC Inhibitors Act Directly on the Frataxin Gene

Figure 5A:
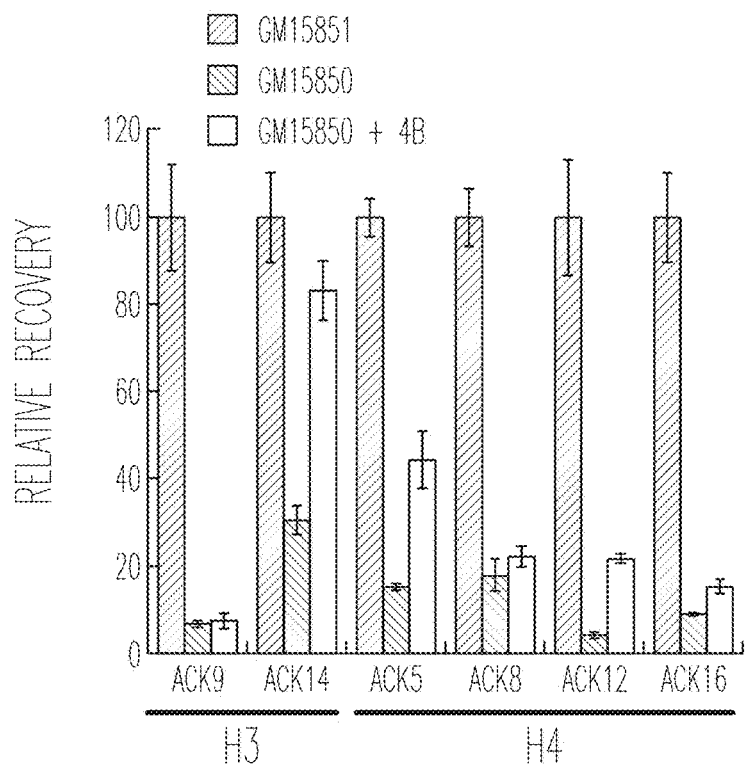
FIG. 5A-5B show bar graphs illustrating the effects of HDAC inhibitors on histone acetylation at the frataxin gene.
Figure 5B:
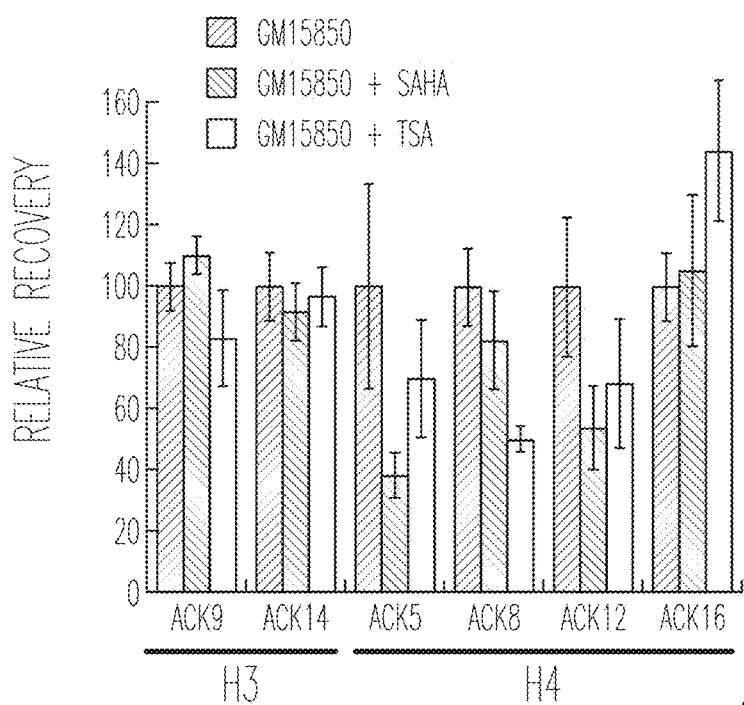

To assess whether the HDAC inhibitors act directly on the histone acetylation state of the frataxin gene, we performed ChIP experiments after treatment of FRDA cells with the HDAC inhibitor 4b (at 5 µM for 96 h) and analyzed histone acetylation on the chromatin region immediately upstream of the GAA repeats. Insufficient yields of cells preclude performing this experiment with lymphocytes from donor blood. Since the region immediately upstream of the GAA repeats showed the most striking difference in histone acetylation between the two cell lines (FIG. 1A), ChIP assays were performed with this probe. Similar ~2.5 to 3-fold increases in frataxin transcription (Table 4) and acetylation at H3-K14, H4-K5 and H4-K12 are observed with 4b in these cells (FIG. 5A). No significant changes in acetylation are observed at H3-K9, H4-K8, or H4-K16. To demonstrate the specificity of the effect of 4b on histone acetylation at the frataxin gene, we performed similar ChIP experiments after treatment of FRDA cells with two common HDAC inhibitors (TSA and SAHA) that had no effect frataxin transcription (FIG. 2B). When the region immediately upstream of the GAA repeats in the frataxin gene was probed after FRDA cells were incubated with these compounds for 96 h, no significant effects on histone acetylation were observed (FIG. 5B). These data suggest that 4b directly inhibits an as yet unidentified HDAC enzyme(s) associated with the frataxin gene, thus resulting in increased levels of acetylated histones by the action of an associated histone acetyltransferase, ultimately leading to increases in frataxin transcription.

Example 9—Additional Selected HDAC Inhibitors

The following additional HDAC inhibitors were synthesized and tested as described above.

KJ-81b: $N^1$-(2-aminophenyl)-$N^7$-(2-methoxyphenyl)heptanediamide
KJ-82b: $N^1$-(4-aminophenyl)-$N^7$-(2-methoxyphenyl)heptanediamide
KJ-102b: $N^1$-(2-aminophenyl)-$N^7$-o-tolylheptanediamide
KJ-106b: $N^1$-(2-aminophenyl)-$N^7$-p-tolylheptanediamide The structures of these compounds and $IC_{50}$ for histone deacetylase inhibition are summarized in Table 5.

TABLE 5

$IC_{50}$ Values of Selected Inhibitors

| Salt ($IC_{50}$) | Structure | Mol. Wt. | Formula | TFA-adduct |
|---|---|---|---|---|
| KJ-81b (37 µM) | 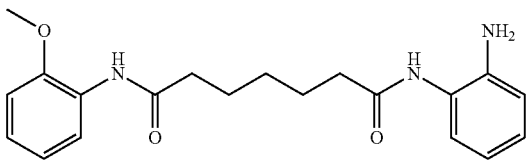 [SMILES: COc1ccccc1NC(=O)CCCCCC(=O)Nc1ccccc1N] | 355.43 g/mol | $C_{20}H_{25}N_3O_3$ | + |

TABLE 5-continued

IC$_{50}$ Values of Selected Inhibitors

| Salt (IC$_{50}$) | Structure | Mol. Wt. | Formula | TFA-adduct |
|---|---|---|---|---|
| KJ-82b (54 µM) | [structure: 2-methoxyphenyl-NH-C(O)-(CH$_2$)$_4$-C(O)-NH-phenyl-4-NH$_2$] | 355.43 g/mol | C$_{20}$H$_{25}$N$_3$O$_3$ | + |
| KJ-102b (not determined) | [structure: 2-methylphenyl-NH-C(O)-(CH$_2$)$_4$-C(O)-NH-phenyl-2-NH$_2$] | 338.43 g/mol | C$_{20}$H$_{25}$N$_3$O$_2$ | + |
| KJ-106b (64 µM) | [structure: 4-methylphenyl-NH-C(O)-(CH$_2$)$_4$-C(O)-NH-phenyl-2-NH$_2$] | 339.43 g/mol | C$_{20}$H$_{25}$N$_3$O$_2$ | + |

REFERENCES

These references are provided for background purposes.

1. Campuzano, V. et al. Friedreich's ataxia: autosomal recessive disease caused by an intronic GAA triplet repeat expansion. *Science* 271, 1423-7 (1996).
2. Pandolfo, M. Friedreich ataxia. *Semin. Pediatr. Neurol.* 10, 163-72 (2003).
3. Bidichandani, S. I., Ashizawa, T. & Patel, P. I. The GAA triplet-repeat expansion in Friedreich ataxia interferes with transcription and may be associated with an unusual DNA structure. *Am. J. Hum. Genet.* 62, 111-21 (1998).
4. Sakamoto, N. et al. Sticky DNA: self-association properties of long GAA.TTC repeats in R.R.Y triplex structures from Friedreich's ataxia. *Mol. Cell* 3, 465-75 (1999).
5. Ohshima, K., Montermini, L., Wells, R. D. & Pandolfo, M. Inhibitory effects of expanded GAA.TTC triplet repeats from intron I of the Friedreich ataxia gene on transcription and replication in vivo. *J. Biol. Chem.* 273, 14588-95 (1998).
6. Grabczyk, E. & Usdin, K. The GAA*TTC triplet repeat expanded in Friedreich's ataxia impedes transcription elongation by T7 RNA polymerase in a length and supercoil dependent manner. *Nucl. Acids Res.* 28, 2815-22 (2000).
7. Saveliev, A., Everett, C., Sharpe, T., Webster, Z. & Festenstein, R. DNA triplet repeats mediate heterochromatin-protein-1-sensitive variegated gene silencing. *Nature* 422, 909-13 (2003).
8. Elgin, S. C. & Grewal, S. I. Heterochromatin: silence is golden. *Curr. Biol.* 13, R895-8 (2003).
9. Grabczyk, E. & Usdin, K. Alleviating transcript insufficiency caused by Friedreich's ataxia triplet repeats. *Nucl. Acids Res.* 28, 4930-7 (2000).
10. Napierala, M., Dere, R., Vetcher, A. & Wells, R. D. Structure-dependent recombination hot spot activity of GAA.TTC sequences from intron 1 of the Friedreich's ataxia gene. *J. Biol. Chem.* 279, 6444-54 (2004).
11. Drummond, D. C. et al. Clinical development of histone deacetylase inhibitors as anticancer agents. *Annu. Rev. Pharmacol. Toxicol.* 45, 495-528 (2005).
12. Di Prospero, N. A. & Fischbeck, K. H. Therapeutics development for triplet repeat expansion diseases. *Nat. Rev. Genet.* 6, 756-65 (2005).
13. Langley, B., Gensert, J. M., Beal, M. F. & Ratan, R. R. Remodeling chromatin and stress resistance in the central nervous system: histone deacetylase inhibitors as novel and broadly effective neuroprotective agents. *Curr. Drug Targets CNS Neurol. Disord.* 4, 41-50 (2005).
14. Peart, M. J. et al. Identification and functional significance of genes regulated by structurally different histone deacetylase inhibitors. *Proc. Natl. Acad. Sci. USA* 102, 3697-702 (2005).
15. Sarsero, J. P. et al. Upregulation of expression from the FRDA genomic locus for the therapy of Friedreich ataxia. *J. Gene Med.* 5, 72-81 (2003).
16. Burnett, R. et al. DNA sequence-specific polyamides alleviate transcription inhibition associated with long GAA-TTC repeats in Friedreich's ataxia. *Proc. Natl. Acad. Sci. USA,* 103, 11497-11502 (2006).
17. Wong, J. C., Hong, R. & Schreiber, S. L. Structural biasing elements for in-cell histone deacetylase paralog selectivity. *J. Am. Chem. Soc.* 125, 5586-7 (2003).
18. Dorer, D. R. & Henikoff, S. Expansions of transgene repeats cause heterochromatin formation and gene silencing in *Drosophila. Cell* 77, 993-1002 (1994).
19. Pohler, J. R. & Lilley, D. M. The interaction of HMG-box proteins with the four-way DNA junction. *Biochem. Soc. Trans.* 25, S647 (1997).
20. Zhao, Y. et al. Acetylation of p53 at lysine 373/382 by the histone deacetylase inhibitor depsipeptide induces expression of p21(Waf1/Cip1). *Mol. Cell. Biol.* 26, 2782-90 (2006).
21. Solomon, J. M. et al. Inhibition of SIRT1 catalytic activity increases p53 acetylation but does not alter cell survival following DNA damage. *Mol. Cell. Biol.* 26, 28-38 (2006).

22. Annunziato, A. T., Frado, L. L., Seale, R. L. & Woodcock, C. L. Treatment with sodium butyrate inhibits the complete condensation of interphase chromatin. *Chromosoma* 96, 132-8 (1988).
23. Tse, C., Sera, T., Wolffe, A. P. & Hansen, J. C. Disruption of higher-order folding by core histone acetylation dramatically enhances transcription of nucleosomal arrays by RNA polymerase III. *Mol. Cell. Biol.* 18, 4629-38 (1998).
24. Annunziato, A. T. & Hansen, J. C. Role of histone acetylation in the assembly and modulation of chromatin structures. *Gene Expr.* 9, 37-61 (2000).
25. Shogren-Knaak, M. et al. Histone H4-K16 acetylation controls chromatin structure and protein interactions. *Science* 311, 844-7 (2006).
26. Strahl, B. D. & Allis, C. D. The language of covalent histone modifications. *Nature* 403, 41-45 (2000).
27. Stewart, M. D., Li, J. & Wong, J. Relationship between histone H3 lysine 9 methylation, transcription repression, and heterochromatin protein 1 recruitment. *Mol. Cell. Biol.* 25, 2525-38 (2005).
28. Litt, M. D., Simpson, M., Gaszner, M., Allis, C. D. & Felsenfeld, G. Correlation between histone lysine methylation and developmental changes at the chicken beta-globin locus. *Science* 293, 2453-5 (2001).
29. Gui, C. Y., Ngo, L., Xu, W. S., Richon, V. M. & Marks, P. A. Histone deacetylase (HDAC) inhibitor activation of p21WAF1 involves changes in promoter-associated proteins, including HDAC1. *Proc. Natl. Acad. Sci. USA* 101, 1241-6 (2004).
30. Sumner, C. J. et al. Valproic acid increases SMN levels in spinal muscular atrophy patient cells. *Ann. Neurol.* 54, 647-54 (2003).
31. Senawong, T. et al. Involvement of the histone deacetylase SIRT1 in chicken ovalbumin upstream promoter transcription factor (COUP-TF)-interacting protein 2-mediated transcriptional repression. *J. Biol. Chem.* 278, 43041-50 (2003).
32. Shestakova, E., Bandu, M. T., Doly, J. & Bonnefoy, E. Inhibition of histone deacetylation induces constitutive derepression of the beta interferon promoter and confers antiviral activity. *J. Virol.* 75, 3444-52 (2001).
33. Suka, N., Suka, Y., Carmen, A. A., Wu, J. & Grunstein, M. Highly specific antibodies determine histone acetylation site usage in yeast heterochromatin and euchromatin. *Mol. Cell* 8, 473-9 (2001).
34. Agalioti, T., Chen, G. & Thanos, D. Deciphering the transcriptional histone acetylation code for a human gene. *Cell* 111, 381-92 (2002).
35. Astrand, C., Klenka, T., Wrange, O. & Belikov, S. Trichostatin A reduces hormone-induced transcription of the MMTV promoter and has pleiotropic effects on its chromatin structure. *Eur. J. Biochem.* 271, 1153-62 (2004).
36. Aron, J. L. et al. Depsipeptide (FR901228) induces histone acetylation and inhibition of histone deacetylase in chronic lymphocytic leukemia cells concurrent with activation of caspase 8-mediated apoptosis and down-regulation of c-FLIP protein. *Blood* 102, 652-8 (2003).
37. Hart, P. E. et al. Antioxidant treatment of patients with Friedreich ataxia: four-year follow-up. *Arch. Neurol.* 62, 621-6 (2005).
38. Ghazizadeh, M. Cisplatin may induce frataxin expression. *J. Nippon Med. Sch.* 70, 367-71 (2003).
39. Turano, M. et al. 3-Nitropropionic acid increases frataxin expression in human lymphoblasts and in transgenic rat PC12 cells. *Neurosci. Lett.* 350, 184-6 (2003).
40. Sturm, B. et al. Recombinant human erythropoietin: effects on frataxin expression in vitro. *Eur. J. Clin. Invest.* 35, 711-7 (2005).
41. Chuma, M. et al. Expression profiling in multistage hepatocarcinogenesis: identification of HSP70 as a molecular marker of early hepatocellular carcinoma. *Hepatology* 37, 198-207 (2003).
42. Pattyn, F., Speleman, F., De Paepe, A. & Vandesompele, J. RTPrimerDB: the real-time PCR primer and probe database. *Nucl. Acids Res.* 31, 122-3 (2003).
43. Luo, R. X., Postigo, A. A. & Dean, D. C. Rb interacts with histone deacetylase to repress transcription. *Cell* 92, 463-73 (1998).

Other Embodiments

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

While the invention has been described in conjunction with the detailed description, the foregoing description is intended to illustrate and not limit the scope of the invention, which is defined by the scope of the appended claims. Other aspects, advantages, and modifications are within the scope of the following claims.

What is claimed is:

1. A method of treating, or delaying the onset of Huntington's disease in a mammal comprising administering to the mammal a compound of formula I in an amount effective to alter the level of histone acetylation in the mammal and increase frataxin mRNA in lymphocytes from Friedreich's ataxia patients, wherein formula I is:

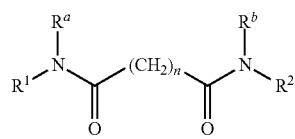

(I)

wherein:
n is 2 to about 10;
$R^1$ is aryl or heteroaryl;
$R^2$ is aryl or heteroaryl;
$R^a$ and $R^b$ are each independently H, alkyl, aryl, heteroaryl, or a nitrogen protecting group;
wherein any alkyl, aryl or heteroaryl is optionally substituted with 1 to 3 substituents selected from the group consisting of hydroxy, amino, nitro, cyano, halo, alkyl, trifluoromethyl, alkoxy, aryl, and $NR^cR^d$;
wherein $R^c$ and $R^d$ are each independently hydrogen, alkyl, or $C(\!=\!O)OR^e$ wherein $R^e$ is H or alkyl;
or a salt thereof.

2. The method of claim 1, further comprising identifying the mammal as one suffering from, or at risk for, Huntington's disease.

3. The method of claim 1, wherein the mammal is a human.

4. The method of claim 1, wherein the compound of formula I has a structure selected from the group consisting of:
a salt of a compound thereof; and
any combination thereof.

* * * * *

UNITED STATES PATENT AND TRADEMARK OFFICE
CERTIFICATE OF CORRECTION

PATENT NO.       : 9,957,225 B2
APPLICATION NO.  : 14/480899
DATED            : May 1, 2018
INVENTOR(S)      : Gottesfeld et al.

Page 1 of 3

It is certified that error appears in the above-identified patent and that said Letters Patent is hereby corrected as shown below:

On the Title Page

Item (*), in "Notice", in Column 1, Line 3, delete "days. days." and insert --days.-- therefor Item (60), in "Related U.S. Application Data", in Column 1, Line 8, delete "60/838,906," and insert --60/838,908,-- therefor On page 2, in Column 1, item (56), under "Other Publications", Line 46, before ""European", delete "06837299.4,"

On page 2, in Column 2, item (56), under "Other Publications", Line 17, delete "Expeditioius" and insert --Expeditious-- therefor On page 2, in Column 2, item (56), under "Other Publications", Line 25, delete "Friedrich" and insert --Friedreich-- therefor On page 2, in Column 2, item (56), under "Other Publications", Line 29, delete "Friedrich's" and insert --Friedreich's-- therefor On page 2, in Column 2, item (56), under "Other Publications", Line 34, delete "design,synthesis,enzyme" and insert --design, synthesis, enzyme-- therefor On page 2, in Column 2, item (56), under "Other Publications", Line 38, delete ".alpha.-substituted" and insert --α-substituted-- therefor In the Specification In Column 5, Line 52, delete "+S⁻," and insert -- -S⁻,-- therefor Signed and Sealed this
Eleventh Day of June, 2019

Andrei Iancu
*Director of the United States Patent and Trademark Office*

CERTIFICATE OF CORRECTION (continued)
U.S. Pat. No. 9,957,225 B2

In Column 7, Line 49, delete "FIG." and insert --FIGS.-- therefor

In Column 8, Line 1, delete "FIG." and insert --FIGS.-- therefor

In Column 8, Line 27, delete "FIG." and insert --FIGS.-- therefor

In Column 8, Line 45, delete "FIG." and insert --FIGS.-- therefor

In Column 9, Line 64, delete "HDA1" and insert --HDAC1-- therefor

In Column 10, Line 32, delete "substitutent" and insert --substituent-- therefor In Column 12, Line 29, delete "100° C." and insert --100 °C.-- therefor In Column 13, Lines 11-17, delete "  " and insert -- -- therefor In Column 16, Line 6, delete "-CH$_2$OC(O)CH$_2$CH(C H$_3$)$_2$," and insert -- -CH$_2$OC(O)CH$_2$CH(CH$_3$)$_2$,-- therefor In Column 17, Line 60, delete "aid" and insert --acid-- therefor In Column 19, Line 26, delete "(4)" and insert --(5)-- therefor In Column 23, Line 2, delete "rt," and insert --r.t.,-- therefor In Column 31, Line 40, delete "55° C." and insert --55 °C.-- therefor In Column 33, Line 3, delete "stifling" and insert --stirring-- therefor In Column 34, Line 21, delete "stifling" and insert --stirring-- therefor In Column 34, Line 42, delete "stifling" and insert --stirring-- therefor In Column 35, Line 13, delete "stifling" and insert --stirring-- therefor In Column 35, Line 39, delete "stifling" and insert --stirring-- therefor In Column 35, Line 61, delete "stifling" and insert --stirring-- therefor In Column 36, Line 22, delete "pardoned" and insert --partitioned-- therefor

CERTIFICATE OF CORRECTION (continued)
U.S. Pat. No. 9,957,225 B2

In Column 36, Line 46, delete "stifling" and insert --stirring-- therefor

In Column 36, Line 67, delete "stifling" and insert --stirring-- therefor

In Column 37, Line 20, delete "stifling" and insert --stirring-- therefor

In Column 37, Line 41, delete "stifling" and insert --stirring-- therefor

In Column 37, Line 61, delete "stifling" and insert --stirring-- therefor

In Column 38, Line 36, delete "stifling" and insert --stirring-- therefor

In Column 38, Line 59, delete "stifling" and insert --stirring-- therefor

In Column 39, Line 12, delete "stifling" and insert --stirring-- therefor

In Column 40, Line 18, delete "µL," and insert --µl,-- therefor

In Column 40, Line 37, delete "55° C." and insert --55 °C.-- therefor

In Column 42, Line 5, delete "stifling" and insert --stirring-- therefor

In Column 43, Line 8, delete "stifling" and insert --stirring-- therefor

In Column 43, Line 29, delete "stifling" and insert --stirring-- therefor

In Column 43, Line 50, delete "stifling" and insert --stirring-- therefor

In Column 44, Line 3, delete "stifling" and insert --stirring-- therefor

In Column 47, Line 2, delete "123" and insert --(123-- therefor

In Column 51, Line 2, delete "mM)" and insert --µM)-- therefor

In Column 55, Line 7, delete "338,43" and insert --339.43-- therefor

```
                          SEQUENCE LISTING

<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
cagaggaaac gctggactct                                                 20

<210> SEQ ID NO 2
<211> LENGTH: 20
<212> TYPE: DNA
<213> ORGANISM: Homo sapiens

<400> SEQUENCE: 2
agccagattt gcttgtttgg                                                 20

<210> SEQ ID NO 3
<211> LENGTH: 20
<212> TYPE: DNA
<213> ORGANISM: Homo sapiens

<400> SEQUENCE: 3
ccccacatac ccaactgctg                                                 20

<210> SEQ ID NO 4
<211> LENGTH: 20
<212> TYPE: DNA
<213> ORGANISM: Homo sapiens

<400> SEQUENCE: 4
gcccgccgct tctaaaattc                                                 20

<210> SEQ ID NO 5
<211> LENGTH: 21
<212> TYPE: DNA
<213> ORGANISM: Homo sapiens

<400> SEQUENCE: 5
gaaacccaaa gaatggctgt g                                               21

<210> SEQ ID NO 6
<211> LENGTH: 20
<212> TYPE: DNA
<213> ORGANISM: Homo sapiens

<400> SEQUENCE: 6
ttccctcctc gtgaaacacc                                                 20

<210> SEQ ID NO 7
<211> LENGTH: 22
```

```
<212> TYPE: DNA
<213> ORGANISM: Homo sapiens

<400> SEQUENCE: 7
ctggaaaaat aggcaagtgt gg                                           22

<210> SEQ ID NO 8
<211> LENGTH: 19
<212> TYPE: DNA
<213> ORGANISM: Homo sapiens

<400> SEQUENCE: 8
caggggtgga agcccaata                                               19

<210> SEQ ID NO 9
<211> LENGTH: 20
<212> TYPE: DNA
<213> ORGANISM: Homo sapiens

<400> SEQUENCE: 9
caccgtcaag gctgagaacg                                              20

<210> SEQ ID NO 10
<211> LENGTH: 20
<212> TYPE: DNA
<213> ORGANISM: Homo sapiens

<400> SEQUENCE: 10
atacccaagg gagccacacc                                              20
```